US009090709B2

(12) United States Patent
Fisher et al.

(10) Patent No.: US 9,090,709 B2
(45) Date of Patent: Jul. 28, 2015

(54) ANTI-SEMA4D ANTIBODIES AND EPITOPES

(71) Applicant: VACCINEX, INC., Rochester, NY (US)

(72) Inventors: Terrence Lee Fisher, Rochester, NY (US); Ernest S. Smith, Ontario, NY (US); Maurice Zauderer, Pittsford, NY (US)

(73) Assignee: Vaccinex, Inc., Rochester, NY (US)

( * ) Notice: Subject to any disclaimer, the term of this patent is extended or adjusted under 35 U.S.C. 154(b) by 0 days.

(21) Appl. No.: 13/828,506

(22) Filed: Mar. 14, 2013

(65) Prior Publication Data
US 2014/0099334 A1 Apr. 10, 2014

Related U.S. Application Data

(60) Provisional application No. 61/616,777, filed on Mar. 28, 2012.

(51) Int. Cl.
C07K 16/28 (2006.01)
C07K 14/705 (2006.01)

(52) U.S. Cl.
CPC ........ C07K 14/70596 (2013.01); C07K 16/2803 (2013.01); C07K 16/2896 (2013.01); C07K 2317/34 (2013.01)

(58) Field of Classification Search
CPC ........... C07K 16/2803; C07K 16/2896; C07K 14/70596; C07K 2317/34
See application file for complete search history.

(56) References Cited

U.S. PATENT DOCUMENTS

| 5,070,192 | A | 12/1991 | Earnshaw et al. |
|---|---|---|---|
| 6,576,754 | B2 | 6/2003 | Hall et al. |
| 6,635,742 | B1 | 10/2003 | Boyle et al. |
| 7,351,803 | B2 | 4/2008 | Johnson et al. |
| 7,700,102 | B2 | 4/2010 | Hall et al. |
| 7,919,246 | B2 | 4/2011 | Lai et al. |
| 7,919,594 | B2 | 4/2011 | Smith et al. |
| 8,067,247 | B2 | 11/2011 | Belin et al. |
| 8,496,938 | B2 | 7/2013 | Smith et al. |
| 8,790,652 | B2 | 7/2014 | Basile et al. |
| 8,816,058 | B2 | 8/2014 | Smith et al. |
| 2002/0037851 | A1 | 3/2002 | Fleckenstein et al. |
| 2003/0158402 | A1 | 8/2003 | Hall et al. |
| 2006/0233793 | A1 | 10/2006 | Belin et al. |
| 2007/0098707 | A1 | 5/2007 | King-Beltran et al. |
| 2008/0219971 | A1 | 9/2008 | Smith et al. |
| 2010/0285036 | A1 | 11/2010 | Smith et al. |
| 2012/0270268 | A1 | 10/2012 | Smith et al. |
| 2013/0095118 | A1 | 4/2013 | Smith et al. |
| 2013/0274449 | A1 | 10/2013 | Smith et al. |
| 2013/0302320 | A1 | 11/2013 | Smith et al. |
| 2014/0072578 | A1 | 3/2014 | Smith et al. |
| 2015/0044219 | A1 | 2/2015 | Evans et al. |

FOREIGN PATENT DOCUMENTS

| WO | WO 93/14125 A1 | 7/1993 |
|---|---|---|
| WO | WO 95/07706 A1 | 3/1995 |
| WO | WO 97/17368 A1 | 5/1997 |
| WO | WO 03/100041 A1 | 4/2003 |
| WO | WO 2004/067034 A1 | 8/2004 |
| WO | WO 2006/110594 A2 | 10/2006 |
| WO | 2008/100995 A1 | 8/2008 |
| WO | WO 2010/129917 A2 | 11/2010 |
| WO | 2013/055922 A1 | 4/2013 |

OTHER PUBLICATIONS

Basile, J. R., et al., "Semaphorin 4D provides a link between axon guidance processes and tumor-induced angiogenesis, "PNAS 103(24):9017-9022, The National Academy of Sciences of the USA, United States (2006).
Billard, C., et al., "Switch in the protein tyrosine phosphatase associated with human CD100 sernaphorin at terminal B-cell differentiation stage," Blood 95(3):965-972, The American Society of Hematology, United States (2000).
Bleck, G. T., "An Alternative Method for the Rapid Generation of Stable, High-Expressing Mammalian Cell Lines," BioProcessing Journal 5 (4):36-42, International Society for BioProcess Technology, United States (2005).
Bougeret, C., et al., "Increased Surface Expression of a Newly Identified 150-kDa Dimer Early After Human T Lymphocyte Activation," The Journal of Immunology 148(2):318-323, The American Association of Immunologists, United States (1992).
Brand, D. D., et al., "Collagen-induced arthritis," Nature Protocols 2(5):1269-1275, Nature Publishing Group, England (2007).
Burgess, W. H., et al., "Possible Dissociation of the Heparin-binding and Mitogenic Activities of Heparin-binding (Acidic Fibroblast) Growth Factor-1 From Its Receptor-binding Activities by Site-directed Mutagenesis of a Single Lysine Residue," The Journal of Cell Biology 111:2129-2138, The Rockefeller University Press, United States (1990).
Chabbert-De Ponnat, I., et al., "Soluble CD100 functions on human monocytes and immature dendritic cells require plexin C1 and plexin B1, respectively," International Immunology 17(4):439-447, The Japanese Society for Immunology, Japan (2005).
Chen, C., . et al., "Generation and Analysis of Random Point Mutations in an Antibody CDR2 Sequence: Many Mutated Antibodies Lose Their Ability to Bind Antigen," J. Exp. Med. 176:855-866, The Rockefeller University Press, United States (1992).
Claesson-Welsh, L., "Novel paths to blood vessel formation," Blood 105(11):4153-4154, The American Society of Hematology, United States (2005).
Conrotto, P., et al., "Sema4D induces angiogenesis through Met Recruitment by Plexin B1" Blood 105(11):4321-4329, The American Society of Hematology, United States (2005).
De Pascalis, R., et al., "Grafting of 'Abbreviated' Complementarity-Determining Regions Containing Specificity-Determining Residues Essential for Ligand Contact to Engineer a Less Immunogenic Humanized Monoclonal Antibody" The Journal of Immunology 169(6):3076-3084. The American Association of Immunologists, Inc., United States (2002).

(Continued)

Primary Examiner — Daniel C Gamett
(74) Attorney, Agent, or Firm — Thompson Coburn LLP

(57) ABSTRACT

The invention relates to epitopes of SEMA4D and to binding agents, such as antibodies, that specifically bind to SEMA4D.

7 Claims, No Drawings

(56) References Cited

OTHER PUBLICATIONS

DeAglio, S., et al., "CD38 and CD100 lead a network of surface receptors relaying positive signals for B-CLL growth and survival," *Blood* 105(8):3042-3050, The American Society of Hematology, United States (2005).

DeLaire, S., et al., "Biological Activity of Soluble CD100. II. Soluble CD100, Similarly to H-SemaIII, Inhibits Immune Cell Migration," *The Journal of Immunology* 166(7):4348-4354, The American Association of Immunologists, United States (2001).

DeLaire, S., et al.,"Inhibition of Immune Cell Migration by Soluble CD100 and H-Sema III Semaphorins," Tissue Antigens, p. 103, vol. 55 (Suppl. 1), Munksgaard, Copenhagen, DK (2000).

Elhabazi, A., et al., "Biological Activity of Soluble CD100. I. The Extracellular Region of CD100 Is Released from the Surface of T Lymphocytes by Regulated Proteolysis," *The Journal of Immunology* 166:4341-4347, The American Association of Immunologists, United States (2001).

Elhabazi, A., et al., "Structure and Function of the Immune Semaphorin CD100/SEMA4D" *Critical Reviews™ in Immunology*, 23(1&2):65-81, Begell House Inc., United States (2003).

Elhabazi, A., et al., "The Human Semaphorin-like Leukocyte Cell Surface Molecule CD100 Associates with a Serine Kinase Activity," *The Journal of Biological Chemistry* 272(38):23515-23520, The American Society for Biochemistry and Molecular Biology, Inc., United States (1997).

Fishwild, D. M., et al., "High-avidity human IgGκ monoclonal antibodies from a novel strain of minilocus transgenic mice," *Nature Biotechnology* 14:845-851, Nature Publishing Group, United States (1996).

Gauld, S. B., et al., "B Cell Antigen Receptor Signaling: Roles in Cell Development and Disease," *Science* 296:1641-1642, The American Association for the Advancement of Science, United States (2002).

Giordano, S., et al., "The Semaphorin 4D receptor controls invasive growth by coupling with Met," *Nature Cell Biology* 4:720-724, Nature Publishing Group, England (2002).

Giraudon, P., et al., "Semaphorin CD100 from Activated T Lymphocytes Induces Process Extension Collapse in Oligodendrocytes and Death of Immature Neural Cells," *The Journal of Immunology*, 172(2):1246-1255, The American Association of Immunologists, Inc., United States (2004).

Giraudon, P., et al., "T-cells in Neuronal Injury and Repair: Semaphorins and Related T-cell Signals," *NeuroMolecular Medicine* 7:207-216, Humana Press Inc., United States (2005).

Goldsby, R. A., et al., "Chapter 20: Autoimmunity," in *Kuby Immunology 4e*: pp. 502-504, W.H. Freeman and Company, United States (2000).

Gouttefangeas, C., et al., "Differential proliferative responses in subsets of human CD28+ cells delineated by BB27 mAb," *International Immunology* 6(3):423-430, The Japanese Society for Immunology, Japan (1993).

Hall, K. T., et al., "Human CD100, a novel leukocyte semaphorin that promotes B-Cell aggregation and differentiation," *Proc. Natl. Acad. Sci* 93:11780-11785, National Academy of Sciences, United States (1996).

Herold, C., et al., "Activation signals are delivered through two distinct epitopes of CD100, a unique 150 kDa human lymphocyte surface structure previously defined by BB18 mAb," *International Immunology* 7(1):1-8, The Japanese Society for Immunology, Japan (1994).

Herold, C., et al., "CD100 defines a newly identified 150-kDa human lymphocyte surface structure," *T-cell antigens—papers T1*:50-51 (1994).

Ishida, I., et al., "Involvement of CD100, A lymphocyte semaphorin, in the activation of the human immune system via CD72: implications for the regulation of immune and inflammatory response," *International Immunology* 15(8):1027-1034, The Japanese Society for Immunology (2003).

Kikutani, H., and Kumanogoh, A., "Semaphorins in Interactions Between T Cells and Antigens-Presenting Cells," *Nature Reviews Immunology* 3:159-167, Nature Publishing Group, England (2003).

Kornbluth, et al., "Novel Tyrosine Kinase Identified by Phosphotyrosine Antibody Screening of cDNA Libraries," *Molecular and Cellular Biology* 8(12):5541-5544, American Society for Microbiology, United States (1988).

Kruger, R. P., et al., "Semaphorins Command Cells to Move," *Nature Reviews Molecular Cell Biology* 6:789-800, Nature Publishing Group, England (2005).

Kumanogoh, A., and Kikutani, H., "Immune semaphorins: a new area of semaphorin research," *Journal of Cell Science* 116:3463-3470, The Company of Biologists Ltd, England (2003).

Kumanogoh, A., and Kikutani, H., "The CD100-CD72 interaction: a novel mechanism of immune regulation," *TRENDS in Immunology* 22(12):670-676, Elsevier Science Ltd., England (2001).

Kumanogoh, A., et al., "Class IV semaphorin Sema4A enhances T-Cell activation and interacts with Tim-2," *Nature* 419:629-633, Nature Publishing Group, England (2002).

Kumanogoh, A., et al., "Identification of CD72 as a Lymphocyte Receptor for the Class IV Semaphorin CD100: a Novel Mechanism for Regulating B Cell Signaling," *Immunity* 13:621-631, Cell Press, United States (2000).

Kumanogoh, A., et al., "Requirement for CD100-CD72 interactions in fine-tuning of B-cell antigen receptor signaling and homeostatic maintenance of the B-cell compartment," *International Immunology* 17(10):1277-1282, The Japanese Society for Immunolgy, Japan (2005).

Kumanogoh, A., et al., "Requirement for the Lymphocyte Semaphorin, CD100, in the Induction of Antigen-Specific T Cells and the Maturation of Dendritic Cells," *The Journal of Immunology* 169(3):1175-1181, The American Association of Immunologists, Inc., United States (2002).

Lamminmaki, U., and Kankare, J. A., "Crystal Structure of a Recombinant Anti-estradiol Fab Fragment in Complex with 17β-Estradiol," *The Journal of Biological Chemistry* 276(39):36687-36694, The American Society for Biochemistry and Molecular Biology Inc., United States (2001).

Lazar, E., et al., "Transforming Growth Factor α: Mutation of Aspartic Acid 47 and Leucine 48 Results in Different Biological Activities," *Molecular and Cellular Biology* 8(3):1247-1252, American Society for Microbiology, United States (1988).

Levin, M. C., et al., "Molecular Mimicry to Neurons Results in Neurological Disease," *Abstract Viewer and Itinerary Planner*: Program No. 415.3., Society for Neuroscience, United States (2002) (Abstract).

Li, D. H., et al., "CD72 Down-Modulates BCR-Induced Signal Transduction and Diminishes Survival in Primary Mature B Lymphocytes," *The Journal of Immunology* 176:5321-5328, The American Association of Immunologists, Inc., United States (2006).

Li, D. H-H., et al., "Modulation of Peripheral B Cell Tolerance by CD72 in Murine Model," *Arthritis & Rheumatism* 58(10):3192-3904, American College of Rheumatology, United States (2008).

Moreau-Fauvarque, C. et al., "The Transmembrane Semaphorin Sema4D/CD100, an Inhibitor of Axonal Growth, Is Expressed on Oligodendrocytes and Upregulated after CNS Lesion," *The Journal of Neuroscience* 23(27):9229-9239, Society for Neuroscience, United States (2003).

Okuno, T., et al., "Roles of Sema4D—Plexin-B1 Interactions in the Central Nervous System for Pathogenesis of Experimental Autoimmune Encephalomyelitis," *The Journal of Immunology* 184(3):1499-1506, The American Association Immunologists, Inc., United States (2010).

Pasterkamp, R. J., "R-Ras fills another GAP in semaphorin signalling," *Trends in Cell Biology* 15(2):61-64, Elsevier Ltd, England (2005).

Rudikoff, S., et al., "Single amino acid substitution altering antigen binding specificity," *Proc. Natl. Acad. Sci. USA* 79:1979-1983, National Academy of Sciences, United States (1982)

Shi, W., et al., "The Class IV Semaphorin CD100 Plays Nonredundant Roles in the Immune System: Defective B and T Cell Activation in CD100-Deficient Mice," *Immunity* 13:633-642, Cell Press, United States (2000).

(56) References Cited

OTHER PUBLICATIONS

Sierra, J. R. et al., "Tumor angiogenesis and progression are enhanced by Sema4D produced by tumor-associated macrophages," *J. Exp. Med.* 205(7):1673-1685, The Rockefeller University Press, United States (2008).

Skolnick, J., and Fetrow, J. S., "From genes to protein structure and function: novel applications of computational approaches in the genomic era," *TIBTECH 18*:34-39, Elsevier Science Ltd., England (2000).

Suzuki, K., et al., "Semaphorins and their receptors in immune cell interactions," *Nat Immunology* 9(1):17-23, Nature Publishing Group, England (2008).

Swierca, J. M., et al., "ErbB-2 and Met Reciprocally Regulate Cellular Signaling via Plexin-B1," *The Journal of Biological Chemistry* 283(4): 1893-1901, The American Society of Biochemistry and Molecular Biology, Inc., United States (2008).

Tamagnone, L., et al., "Plexins Are a Large Family of Receptors for Transmembrane, Secreted, and GPI-Anchored Semaphorins in Vertebrates," *Cell 99*:71-80, Cell Press, United States (1999).

Taniguchi, Y., et al., "Sema4D deficiency results in an increase in the Number of Oligodendrocytes in healthy and injured mouse brains," *Journal of Neuroscience Research* 87(13):2833-2841, Wiley-Liss, Inc., United States (2009).

Turner, L. J., and Hall A., "Plexin-Induced Collapse Assay in COS Cells," *Methods in Enzymology* 406:665-676, Elsevier Inc., United States (2006).

Voet, D., and Voet, J. G., *Biochemistry*, pp. 126-128 and 228-234,John Wiley & Sons, New York, United States (1990).

Wang, X., et al., "Functional soluable CD100/Sema4D released from activated lymphocytes: possible role in normal and pathologic immune responses," *Blood* 97(11):3498-3504, The American Society of Hematology, United States (2001).

Watanabe, C., et al., "Enhanced Immune Responses in Transgenic Mice Expressing a Truncated Form of the Lymphocyte Semaphorin CD100," *The Journal of Immunology* 167(8):4321-4328, The American Association of Immunologists, United States (2001).

Young R. A., and Davis, R. W., "Efficient isolation of genes by using antibody probes," *Proc. Natl. Acad. Sci. USA 80*:1194-1198, National Academy of Sciences, United States (1983).

Zhu, L., et al., "Semaphorin 4D (CD100) Is Expressed on the Surface of Human Platelets and Protrolytically Shed During Platelet Ativation," *Blood 102*(11):Poster Session 155-I, The American Society of Hermatology, United States (2003) (Abstract).

NCBI Entrez, GenBank Report, Accession No. X85991, Adams, R. H., Entry Date Jun. 1995.

NCBI Entrez, GenBank Report, Accession No. AA394007, Wilson, R. K, Entry Date Apr. 1997.

NCBI Entrez, GenBank Report, Accession No. AA262446, Strausberg, R., Entry Date Jan. 1997.

International Search Report and Written Opinion for International Application No. PCT/US10/34116, United States Patent and Trademark Office, United States, mailed on Nov. 8, 2010.

Unverified, machine-generated English language translation of the French Patent Publication No. FR 2686087 A1 (corresponds to International Patent Application No. WO 93/14125 A1), European Patent Office, espacenet database—Worldwide (1993).

Love, C.A., et al., "The ligand-binding face of the semaphorins revealed by the high-resolution crystal structure of SEMA4D," *Nat. Struct. Biol. 10*:843-848, Nature Pub. Co., United States (2003).

Janssen, B.J., et al., "Structural basis of semaphorin-plexin signaling," *Nature 467*: 1118-1122, Nature Publishing Group, English (2010).

International Search Report in International Application No. PCT/US2013/034133, International Searching Authority, United States, mailed on Jun. 17, 2013.

Co-pending U.S. Appl. No. 13/797,048, filed Mar. 12, 2013, inventors Smith, E.S. and Fisher, T.L. (Not Yet Published).

Co-pending U.S. Appl. No. 13/800,713, filed Mar. 13, 2013, inventors Smith, E.S. and Fisher, T.L. (Not Yet Published).

Co-pending U.S. Appl. No. 14/511,679, filed Oct. 10, 2014, Inventor Zauderer, M. (Not Yet Published).

Co-pending U.S. Appl. No. 14/519,965, filed Oct. 21, 2014, Inventors Smith, E., Zauderer, M., Bowers, W., and Jonason, A. (Not Yet Published).

Co-pending U.S. Appl. No. 61/979,384, filed Apr. 14, 2014, Inventors Smith, E., Zauderer, M., Bowers, W., and Jonason, A. (Not Yet Published).

Co-pending U.S. Appl. No. 62/012,805, filed Jun. 16, 2014, Inventors Smith, E., Zauderer, M., Bowers, W., and Jonason, A. (Not Yet Published).

Higgins et al, Enhancing Immune responses to Tumor-associated Antigens, Cancer Biology and Therapy, 2009, pp. 1440-1449, vol. 8 Issue 15.

Lizee et al, "Harnessing the Power of the immune system to target cancer", 2013, Annu rev med pp. 71-90, vol. 64.

ANTI-SEMA4D ANTIBODIES AND EPITOPES

CROSS-REFERENCE TO RELATED APPLICATIONS

This application claims priority benefit to U.S. Provisional Appl. No. 61/616,777, filed on Mar. 28, 2012, the content of which is hereby incorporated by reference in its entirety.

REFERENCE TO SEQUENCE LISTING SUBMITTED ELECTRONICALLY

The content of the electronically submitted sequence listing in ASCII text file (Name "1843_0700001_SequenceListing_ascii.txt"; Size: 47,862 bytes; and Date of Creation: Mar. 14, 2013) filed with the application is incorporated herein by reference in its entirety.

BACKGROUND OF THE INVENTION

Semaphorin 4D (SEMA4D), also known as CD100, is a transmembrane protein (e.g., SEQ ID NO: 1 (human); SEQ ID NO: 2 (murine)) that belongs to the semaphorin gene family. SEMA4D is expressed on the cell surface as a homodimer, but upon cell activation SEMA4D can be released from the cell surface via proteolytic cleavage to generate sSEMA4D, a soluble form of the protein, which is also biologically active. See Suzuki et al., Nature Rev. Immunol. 3:159-167 (2003); Kikutani et al., Nature Immunol. 9:17-23 (2008).

SEMA4D was first identified by generating two mouse monoclonal antibodies, BD16 and BB18, against activated human T cell clones (Herold et al., Int. Immunol. 7:1-8 (1994)). SEMA4D was the first example of a semaphorin expressed in the immune system. SEMA4D is expressed abundantly on the surface of resting T cells, and weakly on resting B cells, monocytes, and professional antigen-presenting cells, such as dendritic cells (DCs). Cellular activation can stimulate up-regulation of surface expression of SEMA4D on B cells and DCs, as well as the generation of sSEMA4D. SEMA4D is thought to function as both a receptor, which signals through its cytoplasmic domain, and as a ligand (Hall et al., PNAS 93:11780-11785 (1996)). One of the receptors identified for SEMA4D is Plexin-B1. Plexin-B1 is expressed in non-lymphoid tissues and is a high affinity (1 nM) receptor for SEMA4D (Tamagnone et al., Cell 99:71-80 (1999)).

SEMA4D is an important mediator of T cell and B cell activation. SEMA4D knockout (SEMA4D−/−) mice have reduced antibody responses to T-dependent antigens and impaired T cell priming. Both of these functions are restored upon the administration of sSEMA4D (Shi et al., Immunity 13:633-642 (2000)).

In addition to the demonstrated effects of SEMA4D on immune cells, SEMA4D also appears to play a direct role in the demyelination and axonal degeneration seen in neuroinflammatory diseases. The pathogenesis of inflammatory demyelinating diseases, such as MS, includes both an inflammatory phase involving immune cells as well as phases of selective demyelination and neurodegeneration. SEMA4D is expressed in central nervous system (CNS) oligodendrocytes and is an inhibitor of axonal regeneration. SEMA4D expression is up-regulated in oligodendrocytes at the periphery of spinal cord lesions (Moreau-Fauvarque et al., J. Neuroscience 23:9229-9239 (2003)). Culturing chronically activated T cells expressing sSEMA4D with human multipotent neural precursors or primary oligodendrocytes from rat brain induces apoptosis and process extension collapse (Giraudon et al., J. Immunol. 172:1246-1255 (2004); Giraudon et al., NeuroMolecular Med. 7:207-216 (2005)). SEMA4D induced apoptosis of neural precursors can be inhibited by the BD16 anti-SEMA4D antibody.

SEMA4D is also a potent pro-angiogenic molecule. Activation of Plexin-B1 through SEMA4D binding transactivates c-Met and promotes the invasive ability of tumor cells and promotes angiogenesis both in vitro and in vivo. Immunohistochemical analysis of SEMA4D in a large tumor sample collection revealed that SEMA4D overexpression is a very frequent event in head and neck, prostate, colon, breast, and lung cancers.

SEMA4D/Plexin-B1 signaling has also been shown to induce migration of endothelial cells and to promote migration of tumor cells (Conrotto et al., Blood 105:4321-4329 (2005); Giordano et al., Nature Cell Biology 4:720-724 (2002)). SEMA4D induced endothelial cell migration is prevented by SEMA4D-blocking antibodies and by SEMA4D knockdown. Knocking down SEMA4D expression in head and neck squamous cell carcioma (HNSCC) cells with SEMA4D short hairpin RNA (shRNA) before grafting into nude mice caused a dramatic reduction in tumor vascularity and tumor growth (Basile et al., PNAS 103:9017-9022 (2006)). Reports have recently pointed to a close correlation between inflammatory infiltration of the tumor stroma and a high vascular grade. SEMA4D is produced by inflammatory cells present in the tumor microenvironment. In an environment lacking SEMA4D, the ability of mouse breast cancer cells to originate tumor masses and metastases was severely impaired, and the source of SEMA4D was tumor associated macrophages (Sierra et al., JEM 205:1673-1685 (2008)).

Thus, there is a further need in the art for SEMA4D neutralizing molecules, e.g., anti-SEMA4D antibodies, for the treatment of cancers and neuroinflammatory diseases.

BRIEF SUMMARY OF THE INVENTION

The invention relates to epitopes of SEMA4D and to binding agents, such as antibodies, that specifically bind to SEMA4D and uses thereof. As well as isolated nucleic acid molecules that encodes the epitopes of SEMA4D and methods of producing the same.

DETAILED DESCRIPTION OF THE INVENTION

I. Definitions

It is to be noted that the term "a" or "an" entity refers to one or more of that entity; for example, "an anti-SEMA4D antibody" is understood to represent one or more anti-SEMA4D antibodies. As such, the terms "a" (or "an"), "one or more," and "at least one" can be used interchangeably herein.

A "binding molecule" or "antigen binding molecule" of the present invention refers in its broadest sense to a molecule that specifically binds an antigenic determinant. In one embodiment, the binding molecule specifically binds to SEMA4D, e.g., to a transmembrane SEMA4D polypeptide of about 150 kDa or a soluble SEMA4D polypeptide of about 120 kDa (commonly referred to as sSEMA4D). In another embodiment, a binding molecule of the invention is an antibody or an antigen binding fragment thereof. In another embodiment, a binding molecule of the invention comprises at least one heavy or light chain CDR of an antibody molecule. In another embodiment, a binding molecule of the invention comprises at least two CDRs from one or more antibody molecules. In another embodiment, a binding molecule of the invention comprises at least three CDRs from one or more antibody molecules. In another embodiment, a binding molecule of the invention comprises at least four CDRs from one or more antibody molecules. In another embodiment, a binding molecule of the invention comprises at least five CDRs from one or more antibody molecules. In another embodiment, a binding molecule of the invention comprises at least six CDRs from one or more antibody molecules.

As used herein, "human" or "fully human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example, in U.S. Pat. No. 5,939,598 by Kucherlapati et al. "Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s).

"Human" or "fully human" antibodies also include "human" or "fully human" antibodies, as described above, that comprise, consist essentially of, or consist of, variants (including derivatives) of antibody molecules (e.g., the VH regions and/or VL regions) described herein, which antibodies or fragments thereof immunospecifically bind to a SEMA4D polypeptide or fragment or variant thereof. Standard techniques known to those of skill in the art can be used to introduce mutations in the nucleotide sequence encoding a human anti-SEMA4D antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1, VHCDR2, VHCDR3, VL region, VLCDR1, VLCDR2, or VLCDR3.

In certain embodiments, the amino acid substitutions are conservative amino acid substitution, discussed further below. Alternatively, mutations can be introduced randomly along all or part of the coding sequence, such as by saturation mutagenesis, and the resultant mutants can be screened for biological activity to identify mutants that retain activity (e.g., the ability to bind a SEMA4D polypeptide, e.g., human, murine, or both human and murine SEMA4D). Such variants (or derivatives thereof) of "human" or "fully human" antibodies can also be referred to as human or fully human antibodies that are "optimized" or "optimized for antigen binding" and include antibodies that have improved affinity to antigen.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al. (1988) Antibodies: A Laboratory Manual (2nd ed.; Cold Spring Harbor Laboratory Press).

As used herein, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL or VK) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs) within these variable domains, of an antibody combine to form the variable region that defines a three dimensional antigen binding site. This quaternary antibody structure forms the antigen binding site present at the end of each arm of the Y. More specifically, the antigen binding site is defined by three CDRs on each of the VH and VL chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see below).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest" and by Chothia and Lesk, *J. Mol. Biol.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues that encompass the CDRs as defined by each of the above cited references are set forth below in Table 1 as a comparison. The exact residue numbers that encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest." Unless otherwise specified, references to the numbering of specific amino acid residue positions in an anti-SEMA4D antibody or antigen-binding fragment, variant, or derivative thereof of the present invention are according to the Kabat numbering system.

Antibodies or antigen-binding fragments, variants, or derivatives thereof of the invention include, but are not limited to, polyclonal, monoclonal, multispecific, human, humanized, primatized, or chimeric antibodies, single-chain antibodies, epitope-binding fragments, e.g., Fab, Fab' and F(ab')$_2$, Fd, Fvs, single-chain Fvs (scFv), disulfide-linked Fvs (sdFv), fragments comprising either a VL or VH domain, fragments produced by a Fab expression library, and anti-idiotypic (anti-Id) antibodies (including, e.g., anti-Id antibodies to anti-SEMA4D antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1, and IgA2, etc.), or subclass of immunoglobulin molecule.

As used herein, the term "heavy chain portion" includes amino acid sequences derived from an immunoglobulin heavy chain. In certain embodiments, a polypeptide comprising a heavy chain portion comprises at least one of: a VH domain, a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain anti-SEMA4D antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody.

The heavy chain portions of a binding molecule for use in the methods disclosed herein may be derived from different immunoglobulin molecules. For example, a heavy chain portion of a polypeptide can comprise a $C_{H1}$ domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain, e.g., a kappa or lambda light chain. Preferably, the light chain portion comprises at least one of a VL or CL domain.

As used herein, the term "chimeric antibody" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g., mouse or primate) and the constant region is human.

As used herein, the term "engineered antibody" refers to an antibody in which the variable domain in either the heavy or light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable domain to transfer the antigen binding capacity of one variable domain to another. Rather, it may only be necessary to transfer those residues that are necessary to maintain the activity of the target binding site.

It is further recognized that the framework regions within the variable domain in a heavy or light chain, or both, of a humanized antibody may comprise solely residues of human origin, in which case these framework regions of the humanized antibody are referred to as "fully human framework regions" (for example, MAb VX15/2503, disclosed in U.S. Patent Appl. Publication No. US 2010/0285036 A1 as MAb 2503, incorporated herein by reference in its entirety). Alternatively, one or more residues of the framework region(s) of the donor variable domain can be engineered within the corresponding position of the human framework region(s) of a variable domain in a heavy or light chain, or both, of a humanized antibody if necessary to maintain proper binding or to enhance binding to the SEMA4D antigen. A human framework region that has been engineered in this manner would thus comprise a mixture of human and donor framework residues, and is referred to herein as a "partially human framework region."

For example, humanization of an anti-SEMA4D antibody can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent or mutant rodent CDRs or CDR sequences for the corresponding sequences of a human anti-SEMA4D antibody. See also U.S. Pat. Nos. 5,225,539; 5,585,089; 5,693,761; 5,693,762; 5,859,205; herein incorporated by reference. The resulting humanized anti-SEMA4D antibody would comprise at least one rodent or mutant rodent CDR within the fully human framework regions of the variable domain of the heavy and/or light chain of the humanized antibody. In some instances, residues within the framework regions of one or more variable domains of the humanized anti-SEMA4D antibody are replaced by corresponding non-human (for example, rodent) residues (see, for example, U.S. Pat. Nos. 5,585,089; 5,693, 761; 5,693,762; and 6,180,370), in which case the resulting humanized anti-SEMA4D antibody would comprise partially human framework regions within the variable domain of the heavy and/or light chain.

Furthermore, humanized antibodies can comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the CDRs correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., Nature 331:522-525 (1986); Riechmann et al., Nature 332:323-329 (1988); and Presta, Curr. Op. Struct. Biol. 2:593-596 (1992); herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225, 539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

II. Target Polypeptide Description

As used herein, the terms "semaphorin-4D," "SEMA4D" and "SEMA4D polypeptide" are used interchangeably, as are "SEMA4D" and "Sema4D." In certain embodiments, SEMA4D is expressed on the surface of or secreted by a cell. In another embodiment, SEMA4D is membrane bound. In another embodiments, SEMA4D is soluble, e.g., sSEMA4D. In another embodiments, SEMA4D may include a full-sized SEMA4D or a fragment thereof, or a SEMA4D variant polypeptide, wherein the fragment of SEMA4D or SEMA4D variant polypeptide retains some or all functional properties of the full-sized SEMA4D.

The full-sized human SEMA4D protein is a homodimeric transmembrane protein consisting of two polypeptide chains of 150 kDa. SEMA4D belongs to the semaphorin family of cell surface receptors and is also referred to as CD100. Both human and mouse SEMA4D/Sema4D are proteolytically cleaved from their transmembrane form to generate 120-kDa soluble forms, indicating the existence of two Sema4D isoforms (Kumanogoh et al., J. Cell Science 116(7):3464 (2003)). Semaphorins consist of soluble and membrane-bound proteins that were originally defined as axonal-guidance factors during development which play an important role in establishing precise connections between neurons and their appropriate target. Structurally considered a class IV semaphorin, SEMA4D consists of an amino-terminal signal sequence followed by a characteristic 'Sema' domain, which contains 17 conserved cysteine residues, an Ig-like domain, a lysine-rich stretch, a hydrophobic transmembrane region, and a cytoplasmic tail.

Each polypeptide chain of SEMA4D includes a signal sequence of about 13 amino acids followed by a semaphorin domain of about 512 amino acids, an immunoglobulin-like (Ig-like) domain of about 65 amino acids, a lysine-rich stretch of 104 amino acids, a hydrophobic transmembrane region of about 19 amino acids, and a cytoplasmic tail of 110 amino acids. A consensus site for tyrosine phosphorylation in the cytoplasmic tail supports the predicted association of SEMA4D with a tyrosine kinase (Schlossman, et al., Eds. (1995) Leucocyte Typing V (Oxford University Press, Oxford).

SEMA4D is known to have at least two receptors. One of the receptors, Plexin-B1, is expressed in non-lymphoid tissues and has been shown to be a high affinity (1 nM) receptor for SEMA4D (Tamagnone et al., *Cell* 99:71-80 (1999)). In certain embodiments the endothelial cells express Plexin-B1. SEMA4D stimulation of Plexin-B1 signaling has been shown to induce growth cone collapse of neurons, and to induce process extension collapse and apoptosis of oligodendrocytes (Giraudon et al., *J. Immunol.* 172:1246-1255 (2004); Giraudon et al., *NeuroMolecular Med.* 7:207-216 (2005)). After binding to SEMA4D, Plexin-B1 signaling mediates the inactivation of R-Ras, leading to a decrease in the integrin mediated attachment to the extracellular matrix, as well as to activation of RhoA, leading to cell collapse by reorganization of the cytoskeleton. See Kruger et al., *Nature Rev. Mol. Cell Biol.* 6:789-800 (2005); Pasterkamp, *TRENDS in Cell Biology* 15:61-64 (2005)).

In lymphoid tissues CD72 is utilized as a low affinity (300 nM) SEMA4D receptor (Kumanogoh et al., *Immunity* 13:621-631 (2000)). B cells and APCs express CD72, and anti-CD72 antibodies have many of the same effects as sSEMA4D, such as enhancement of CD40-induced B cell responses and B cell shedding of CD23. CD72 is thought to act as a negative regulator of B cell responses by recruiting the tyrosine phosphatase SHP-1, which can associate with many inhibitory receptors. Interaction of SEMA4D with CD72 results in the dissociation of SHP-1, and the loss of this negative activation signal. SEMA4D has been shown to promote T cell stimulation and B cell aggregation and survival in vitro. The addition of SEMA4D-expressing cells or sSEMA4D enhances CD40-induced B cell proliferation and immunoglobulin production in vitro, and accelerates in vivo antibody responses (Ishida et al., *Inter. Immunol.* 15:1027-1034 (2003); Kumanogoh and H. Kukutani, *Trends in Immunol.* 22:670-676 (2001)). sSEMA4D enhances the CD40 induced maturation of DCs, including up-regulation of costimulatory molecules and increased secretion of IL-12. In addition, sSEMA4D can inhibit immune cell migration, which can be reversed by addition of blocking anti-SEMA4D antibodies (Elhabazi et al., *J. Immunol.* 166:4341-4347 (2001); Delaire et al., *J. Immunol.* 166:4348-4354 (2001)).

Sema4D is expressed at high levels in lymphoid organs, including the spleen, thymus, and lymph nodes, and in non-lymphoid organs, such as the brain, heart, and kidney. In lymphoid organs, Sema4D is abundantly expressed on resting T cells but only weakly expressed on resting B cells and antigen-presenting cells (APCs), such as dendritic cells (DCs). Cellular activation increases the surface expression of SEMA4D as well as the generation of soluble SEMA4D (sSEMA4D).

The expression pattern of SEMA4D suggests that it plays an important physiological as well as pathological role in the immune system. SEMA4D has been shown to promote B cell activation, aggregation and survival; enhance CD40-induced proliferation and antibody production; enhance antibody response to T cell dependent antigens; increase T cell proliferation; enhance dendritic cell maturation and ability to stimulate T cells; and is directly implicated in demyelination and axonal degeneration (Shi et al., *Immunity* 13:633-642 (2000); Kumanogoh et al., *J Immunol* 169:1175-1181 (2002); and Watanabe et al., *J Immunol* 167:4321-4328 (2001)).

SEMA4D knock out (SEMA4D−/−) mice have provided additional evidence that SEMA4D plays an important role in both humoral and cellular immune responses. There are no known abnormalities of non-lymphoid tissues in SEMA4D−/− mice. Dendritic cells (DCs) from the SEMA4D−/− mice have poor allostimulatory ability and show defects in expression of costimulatory molecules, which can be rescued by the addition of sSEMA4D. Mice deficient in SEMA4D (SEMA4D−/−) fail to develop experimental autoimmune encephalomyelitis induced by myelin oligodendrocyte glycoprotein peptide, because myelin oligodendrocyte glycoprotein-specific T cells are poorly generated in the absence of SEMA4D (Kumanogoh et al., *J Immunol* 169:1175-1181 (2002)). A significant amount of soluble SEMA4D is also detected in the sera of autoimmunity-prone MRL/lpr mice (model of systemic autoimmune diseases such as SLE), but not in normal mice. Further, the levels of sSEMA4D correlate with levels of auto-antibodies and increase with age (Wang et al., *Blood* 97:3498-3504 (2001)). Soluble SEMA4D has also been shown to accumulate in the cerebral spinal fluid and sera of patients with demyelinating disease, and sSEMA4D induces apoptosis of human pluripotent neural precursors (Dev cells), and both inhibits process extension and induces apoptosis of rat oligodendrocytes in vitro (Giraudon et al., *J Immunol* 172(2):1246-1255 (2004)). This apoptosis was blocked by an anti-SEMA4D MAb.

III. Anti-SEMA4D Antibodies

Antibodies that bind SEMA4D have been described in the art. See, for example, US Publ. Nos. 2008/0219971 A1, US 2010/0285036 A1, and US 2006/0233793 A1, International Patent Applications WO 93/14125, WO 2008/100995, and WO 2010/129917, and Herold et al., *Int. Immunol.* 7(1): 1-8 (1995), each of which is herein incorporated in its entirety by reference.

The invention generally relates to an antibody which specifically binds to SEMA4D, or an antigen-binding fragment, variant, or derivative thereof. In certain embodiments, the antibody binds to an epitope of the present application. In certain embodiments, the antibody blocks the interaction of SEMA4D with one or more of its receptors, e.g., Plexin-B1. In other embodiments, the antibody prevents the dimerization of SEMA4D. Anti-SEMA4D antibodies having these properties can be used in the methods provided herein. Antibodies that can be used include, but are not limited to MAbs VX15/2503, 67, and 76 and antigen-binding fragments, variants, or derivatives thereof which are fully described in US 2010/0285036 A1. Additional antibodies which can be used in the methods provided herein include the BD16 and BB18 antibodies described in US 2006/0233793 A1 as well as antigen-binding fragments, variants, or derivatives thereof; or any of MAb 301, MAb 1893, MAb 657, MAb 1807, MAb 1656, MAb 1808, Mab 59, MAb 2191, MAb 2274, MAb 2275, MAb 2276, MAb 2277, MAb 2278, MAb 2279, MAb 2280, MAb 2281, MAb 2282, MAb 2283, MAb 2284, and MAb 2285, as well as any fragments, variants or derivatives thereof as described in US 2008/0219971 A1. In certain embodiments an anti-SEMA4D antibody for use in the methods provided herein binds human, murine, or both human and murine SEMA4D. Also useful are antibodies which bind to the same epitope as any of the aforementioned antibodies and/or antibodies which competitively inhibit any of the aforementioned antibodies.

In certain embodiments, an anti-SEMA4D antibody or antigen-binding fragment, variant, or derivative thereof useful in the methods provided herein has an amino acid sequence that has at least about 80%, about 85%, about 88%, about 89%, about 90%, about 91%, about 92%, about 93%, about 94%, or about 95% sequence identity to the amino acid sequence for a reference anti-SEMA4D antibody molecule, for example those described above. In a further embodiment, the binding molecule shares at least about 96%, about 97%, about 98%, about 99%, or 100% sequence identity to a reference antibody.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to CDR1, CDR2 or CDR3 of SEQ ID NO: 3 or 4.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to SEQ ID NO: 5, SEQ ID NO: 6, or SEQ ID NO: 7.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence identical, except for 1, 2, 3, 4, or 5 conservative amino acid substitutions, to SEQ ID NO: 5, SEQ ID NO: 6, or SEQ ID NO: 7.

In another embodiment, an anti-SEMA4D antibody or antigen-binding fragment, variant, or derivative thereof useful in the methods provided herein comprises, consists essentially of, or consists of a VH domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 3 or SEQ ID NO: 4, wherein an anti-SEMA4D antibody comprising the encoded VH domain specifically or preferentially binds to SEMA4D.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to CDR1, CDR2 or CDR3 of SEQ ID NO: 8 or 9.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to SEQ ID NO: 10, SEQ ID NO: 11, or SEQ ID NO: 12.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence identical, except for 1, 2, 3, 4, or 5 conservative amino acid substitutions, to SEQ ID NO: 10, SEQ ID NO: 11, or SEQ ID NO: 12.

In a further embodiment, an anti-SEMA4D antibody or antigen-binding fragment, variant, or derivative thereof useful in the methods provided herein comprises, consists essentially of, or consists of a VL domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 8 or SEQ ID NO: 9, wherein an anti-SEMA4D antibody comprising the encoded VL domain specifically or preferentially binds to SEMA4D.

Also included for use in the methods provided herein are polypeptides encoding anti-SEMA4D antibodies, or antigen-binding fragments, variants, or derivatives thereof as described herein, polynucleotides encoding such polypeptides, vectors comprising such polynucleotides, and host cells comprising such vectors or polynucleotides, all for producing anti-SEMA4D antibodies, or antigen-binding fragments, variants, or derivatives thereof for use in the methods described herein.

Suitable biologically active variants of the anti-SEMA4D antibodies of the invention can be used in the methods of the present invention. Such variants will retain the desired binding properties of the parent anti-SEMA4D antibody. Methods for making antibody variants are generally available in the art.

Methods for mutagenesis and nucleotide sequence alterations are well known in the art. See, for example, Walker and Gaastra, eds. (1983) Techniques in Molecular Biology (MacMillan Publishing Company, New York); Kunkel, *Proc. Natl. Acad. Sci. USA* 82:488-492 (1985); Kunkel et al., *Methods Enzymol.* 154:367-382 (1987); Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in Atlas of Protein Sequence and Structure (Natl. Biomed. Res. Found., Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. Conservative substitutions, such as exchanging one amino acid with another having similar properties, may be preferred. Examples of conservative amino acid substitutions as taught by the PAM 250 matrix of the Dayhoff et al. model include, but are not limited to, Gly ↔ Ala, Val↔ Ile↔ Leu, Asp↔ Glu, Lys↔ Arg, Asn ↔ Gln, and Phe↔ Trp↔ Tyr.

In constructing variants of the anti-SEMA4D binding molecule, e.g., an antibody or antigen-binding fragment thereof, polypeptides of interest, modifications are made such that variants continue to possess the desired properties, e.g., being capable of specifically binding to a SEMA4D, e.g., human, murine, or both human and murine SEMA4D, e.g., expressed on the surface of or secreted by a cell and having SEMA4D blocking activity, as described herein. Obviously, any mutations made in the DNA encoding the variant polypeptide must not place the sequence out of reading frame and preferably will not create complementary regions that could produce secondary mRNA structure. See EP Patent Application Publication No. 75,444.

Methods for measuring anti-SEMA4D binding molecule, e.g., an antibody or antigen-binding fragment, variant, or derivative thereof, binding specificity include, but are not limited to, standard competitive binding assays, assays for monitoring immunoglobulin secretion by T cells or B cells, T cell proliferation assays, apoptosis assays, ELISA assays, and the like. See, for example, such assays disclosed in WO 93/14125; Shi et al., *Immunity* 13:633-642 (2000); Kumanogoh et al., *J Immunol* 169:1175-1181 (2002); Watanabe et al., *J Immunol* 167:4321-4328 (2001); Wang et al., *Blood*

97:3498-3504 (2001); and Giraudon et al., *J Immunol* 172(2): 1246-1255 (2004), all of which are herein incorporated by reference.

When discussed herein whether any particular polypeptide, including the epitopes, constant regions, CDRs, VH domains, or VL domains disclosed herein, is at least about 65%, about 70%, about 75%, about 80%, about 85%, about 90%, about 91%, about 92%, about 93%, about 94%, about 95%, about 96%, about 97%, about 98%, about 99%, or even about 100% identical to another polypeptide, the % identity can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) Adv. Appl. Math. 2:482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

For purposes of the present invention, percent sequence identity may be determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) Adv. Appl. Math. 2:482-489. A variant may, for example, differ from a reference anti-SEMA4D antibody (e.g., MAb VX15/2503, 67 or 76, each disclosed in U.S. Patent Appl. Publication No. US 2010/0285036 A1, which is incorporated herein by reference in its entirety) by as few as 1 to 15 amino acid residues, as few as 1 to 10 amino acid residues, such as 6-10, as few as 5, as few as 4, 3, 2, or even 1 amino acid residue.

The constant region of an anti-SEMA4D antibody can be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

In certain anti-SEMA4D antibodies or fragments, variants or derivatives thereof useful in the methods provided herein, the Fc portion can be mutated to decrease effector function using techniques known in the art. For example, the deletion or inactivation (through point mutations or other means) of a constant region domain can reduce Fc receptor binding of the circulating modified antibody thereby increasing tumor localization. In other cases, constant region modifications consistent with the instant invention moderate complement binding and thus reduce the serum half-life. Yet other modifications of the constant region can be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, can easily be measured and quantified using well known immunological techniques without undue experimentation.

Anti-SEMA4D antibodies for use in the methods provided herein include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, etc. Additionally, the derivative can contain one or more non-classical amino acids.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence (e.g., an antibody coding sequence or an epitope coding sequence), such as by saturation mutagenesis, and the resultant mutants can be screened for biological activity to identify mutants that retain activity (e.g., the ability to bind an anti-SEMA4D polypeptide, to block SEMA4D interaction with its receptor, or to bind an anti-SEMA4D antibody or binding fragment thereof).

For example, it is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage, or improve a hybridoma's antibody production. Alternatively, non-neutral missense mutations may alter an antibody's ability to bind antigen. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to immunospecifically bind at least one epitope of a SEMA4D polypeptide) can be determined using techniques described herein or by routinely modifying techniques known in the art.

In certain embodiments, the anti-SEMA4D antibodies for use in the methods provided herein comprise at least one optimized complementarity-determining region (CDR). By "optimized CDR" is intended that the CDR has been modified and optimized to improve binding affinity and/or anti-SEMA4D activity that is imparted to an anti-SEMA4D antibody comprising the optimized CDR. "Anti-SEMA4D activity" or "SEMA4D blocking activity" can include activity which modulates one or more of the following activities associated with SEMA4D: B cell activation, aggregation and survival; CD40-induced proliferation and antibody production; antibody response to T cell dependent antigens; T cell or other immune cell proliferation; dendritic cell maturation; demyelination and axonal degeneration; apoptosis of pluripotent neural precursors and/or oligodendrocytes; induction of endothelial cell migration; inhibition of spontaneous monocyte migration; binding to cell surface Plexin-B1 or other receptor, or any other activity association with soluble SEMA4D or SEMA4D that is expressed on the surface of SEMA4D+ cells. Anti-SEMA4D activity can also be attributed to a decrease in incidence or severity of diseases associated with SEMA4D expression, including, but not limited to, certain types of cancers including lymphomas, autoimmune diseases, inflammatory diseases including central nervous system (CNS) and peripheral nervous system (PNS) inflammatory diseases, transplant rejections, and invasive angiogenesis. Examples of optimized antibodies based on murine anti-SEMA4D MAbs BD16 and BB18, were described in US Publ. No. 2008/0219971 A1, International Patent Application WO 93/14125 and Herold et al., *Int. Immunol.* 7(1): 1-8 (1995), each of which are herein incorporated by reference in their entirety. The modifications may involve replacement of amino acid residues within the CDR such that an anti-SEMA4D antibody retains specificity for the SEMA4D antigen and has improved binding affinity and/or improved anti-SEMA4D activity.

IV. Binding Characteristics of Anti-SEMA4D Antibodies

The invention generally relates to a binding agent, such as an antibody which specifically binds to SEMA4D, or an antigen-binding fragment, variant, or derivative thereof. In certain embodiments, the binding agent binds to an epitope of the present application. The nucleotide and amino acid sequences for one variant of SEMA4D are set forth in SEQ ID NO:13 and SEQ ID NO:14, respectively, and for another variant of SEMA4D are set forth in SEQ ID NO: 15 and SEQ ID NO: 16. In some embodiments, the anti-SEMA4D antibody designated as VX15/2503 is provided. Antibodies that have the binding characteristics of antibody VX15/2503 are also disclosed herein. Such antibodies include, but are not limited to, antibodies that compete in competitive binding assays with VX15/2503, as well as antibodies that bind to an epitope (defined below) capable of binding VX15/2503. Methods for assessing whether antibodies have the same or similar binding characteristics include traditional quantitative methods such as, for example, determining and comparing antibody affinity or avidity for the antigenic epitope (e.g., SEMA4D peptide). Other exemplary methods for comparing the binding characteristics of antibodies include competitive western blotting, enzyme immunoassays, ELISA, and flow cytometry. Methods for assessing and comparing antibody-antigen binding characteristics are well known in the art. Variants and fragments of VX15/2503 that retain the ability to specifically bind to SEMA4D are also provided.

Anti-SEMA4D antibodies, or antigen-binding fragments, variants, or derivatives thereof disclosed herein may be described or specified in terms of the epitope(s) or portion(s) of an antigen, e.g., a target polypeptide disclosed herein (e.g., SEMA4D) that they recognize or specifically bind. The portion of a target polypeptide that specifically interacts with the antigen binding domain of an antibody is an "epitope," or an "antigenic determinant."

In certain embodiments, an "epitope" is intended to be the part of an antigenic molecule which is used to produce an antibody and/or to which an antibody will specifically bind. A "SEMA4D epitope" comprises the part of the SEMA4D protein to which an anti-SEMA4D antibody binds. Epitopes can comprise linear amino acid residues (i.e., residues within the epitope that are arranged sequentially one after another in a linear fashion), nonlinear amino acid residues (referred to herein as "nonlinear epitopes" or "conformational epitopes"; these epitopes are not arranged sequentially), or both linear and nonlinear amino acid residues. Nonlinear epitopes or conformational epitopes can also include amino acid residues that contribute to the overall conformation of the recognition structure of the antibody, but do not necessarily bind the antibody. Typically, epitopes are short amino acid sequences, e.g. about five amino acids in length. Systematic techniques for identifying epitopes are known in the art and are described, for example, in the examples set forth below.

A target polypeptide can comprise a single epitope, but typically comprises at least two epitopes, and can include any number of epitopes, depending on the size, conformation, and type of antigen. Furthermore, it should be noted that an "epitope" on a target polypeptide may be or may include non-polypeptide elements, e.g., an epitope may include a carbohydrate side chain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. A peptide or polypeptide epitope recognized by anti-SEMA4D antibodies of the present invention may contain a sequence of at least 4, at least 5, at least 6, at least 7, more preferably at least 8, at least 9, at least 10, at least 15, at least 20, at least 25, or between about 15 to about 30 contiguous or non-contiguous amino acids of SEMA4D.

In certain embodiments, the epitope has at least 80%, 85%, 90%, 95%, or 100% identity to a target polypeptide amino acid sequence (e.g., the sequence set forth in SEQ ID NO:18, SEQ ID NO:20 or SEQ ID NO:22).

In certain embodiments, the epitope is identical to a target polypeptide amino acid sequence (e.g., the sequence set forth in SEQ ID NO:18, SEQ ID NO:20, or SEQ ID NO:22) except for 4, 3, 2, 1 or 0 amino acid substitutions. In another embodiment, the epitope is identical to a target polypeptide amino acid sequence (e.g., the sequence set forth in SEQ ID NO:18, SEQ ID NO:20, or SEQ ID NO:22) except for conservative amino acid substitutions (e.g., 10, 9, 8, 7, 6, 5, 4, 3, 2, 1 or 0 conservative amino acid substitutions).

In certain embodiments, the epitope comprises a sequence set forth in SEQ ID NO:18, SEQ ID NO:20, or SEQ ID NO:22. In another embodiment, the epitope is the sequence set forth in SEQ ID NO:18, SEQ ID NO:20, or SEQ ID NO:22. In certain embodiments, the epitope is a linear epitope. In certain embodiments, the epitope is a conformational epitope.

In certain embodiments, the epitope comprises, consists essentially of, or consists of LKVPVFYALFTPQLNNV (SEQ ID NO: 18, corresponding to residues 304 through 320 of the full-length SEMA4D amino acid sequence set forth in SEQ ID NO:1), KWTSFLKARLIASRP (SEQ ID NO: 20, corresponding to residues 270 through 284 of the full-length SEMA4D amino acid sequence set forth in SEQ ID NO:1, wherein position 281 can be a cysteine or an alanine), or EFVFRVLIPRIARV (SEQ ID NO:22; corresponding to residues 243 through 256 of the full-length SEMA4D amino acid sequence set forth in SEQ ID NO:1). In certain embodiments, the epitope comprises one or more of the amino acid sequences set forth in SEQ ID NO: 18, 20 and 22. In certain embodiments, the epitope is a discontinuous epitope comprised in the domain spanning amino acid residues 243 to 320 of SEQ ID NO:1.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain, more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant ($K_D$) that is less than the antibody's $K_D$ for the second epitope. In another non-limiting example, an antibody may be considered to bind a first epitope preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with a k(off) that is at least one order of magnitude less than the antibody's k(off) for the second epitope. In another non-limiting example, an antibody may be considered to bind a first epitope preferentially if it binds the first epitope with a k(off) that is at least two orders of magnitude less than the antibody's k(off) for the second epitope. An antibody or antigen-binding fragment, variant, or derivative disclosed herein may be said to bind a target polypeptide disclosed herein (e.g., SEMA4D, e.g., human, murine, or both human and murine SEMA4D) or a fragment or variant thereof with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. More preferably, an antibody of the invention may be said to bind a target polypeptide disclosed herein (e.g., SEMA4D, e.g., human, murine, or both human and murine SEMA4D) or a fragment or variant thereof with an off rate (k(off)) less than or equal to $5\times10^{-4}$ sec$^{-1}$, $10^{-4}$ sec$^{-1}$, $5\times10^{-5}$ sec$^{-1}$, or $10^{-5}$ sec$^{-1}$, $5\times10^{-6}$ sec$^{-1}$, $10^{-6}$ sec$^{-1}$, $5\times10^{-7}$ sec$^{-1}$ or $10^{-7}$ sec$^{-1}$.

An antibody or antigen-binding fragment, variant, or derivative disclosed herein may be said to bind a target polypeptide disclosed herein (e.g., SEMA4D, e.g., human, murine, or both human and murine SEMA4D) or a fragment or variant thereof with an on rate (k(on)) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$ sec$^{-1}$. More preferably, an antibody of the invention may be said to bind a target polypeptide disclosed herein (e.g., SEMA4D, e.g., human, murine, or both human and murine SEMA4D) or a fragment or variant thereof with an on rate (k(on)) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$ M$^{-1}$ sec$^{-1}$.

An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al. (1988) Antibodies: A Laboratory Manual (Cold Spring Harbor Laboratory Press, 2nd ed.) pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Anti-SEMA4D antibodies or antigen-binding fragments, variants, or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Anti-SEMA4D binding molecules, e.g., antibodies or antigen-binding fragments, variants or derivatives thereof, of the invention may also be described or specified in terms of their binding affinity to a polypeptide of the invention, e.g., SEMA4D, e.g., human, murine, or both human and murine SEMA4D. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M. In certain embodiments, the anti-SEMA4D binding molecule, e.g., an antibody or antigen binding fragment thereof, of the invention binds human SEMA4D with a Kd of about $5\times10^{-9}$ to about $6\times10^{-9}$. In another embodiment, the anti-SEMA4D binding molecule, e.g., an antibody or antigen binding fragment thereof, of the invention binds murine SEMA4D with a Kd of about $1\times10^{-9}$ to about $2\times10^{-9}$.

Antibodies that recognize the epitope of anti-SEMA4D antibody VX15/2503 are provided herein. In some embodiments, the epitope sequence can comprise at least one of, and in some embodiments, all of, the amino acid sequences encoded by SEQ ID NO: 17, 19 and 21. In these embodiments, the epitope sequence can comprise at least one of, and in some embodiments, all of, SEQ ID NO: 18, 20 and 22. In some of these embodiments, the epitope comprises at least one of, and in some embodiments, all of, the following sequences: SEQ ID NO:18 at the amino acid residue positions corresponding to positions 304 through 320 of SEQ ID NO:1, 14 or 16; SEQ ID NO:20 at the amino acid residue positions corresponding to positions 270 through 284 of SEQ ID NO:1, 14 or 16, wherein the cysteine at position 281 is replaced with alanine; and SEQ ID NO:22 at the amino acid residue positions corresponding to positions 243 through 256 of SEQ ID NO: 1, 14 or 16.

The invention may also encompass isolated polypeptides comprising an epitope for binding an anti-SEMA4D antibody of the invention. These polypeptides correspond to a portion of the SEMA4D antigen that binds to antibody VX15/2503. Such polypeptides find use in methods for producing or detecting antibodies that selectively bind to SEMA4D. The ability of a polypeptide to be used in the production or detection of antibodies is referred to herein as "antigenic activity." For example, in one embodiment, the isolated polypeptide comprises an epitope for binding an anti-SEMA4D antibody that comprises at least one of, and in some embodiments, all of, SEQ ID NO: 18, 20 and 22. In some of these embodiments, the epitope comprises at least one of, and in some embodiments, all of, the following sequences: SEQ ID NO:18 at the amino acid residue positions corresponding to positions 304 through 320 of SEQ ID NO:1, 14 or 16; SEQ ID NO:20 at the amino acid residue positions corresponding to positions 270 through 284 of SEQ ID NO:1, 14 or 16, wherein the cysteine at position 281 is replaced with alanine; and SEQ ID NO:22 at the amino acid residue positions corresponding to positions 243 through 256 of SEQ ID NO:1, 14 or 16.

In accordance with some embodiments, the invention may also encompass variants and/or fragments of the sequences set forth in SEQ ID NO: 18, 20 and/or 22, or combinations thereof that retain the antigenic activity of the original polypeptide. The invention may, in some embodiments, include isolated nucleic acid molecules that encode a polypeptide that comprises an epitope sequence set forth in SEQ ID NO: 18, 20 or 22, or combinations thereof, and variants and/or fragments thereof.

In accordance with some embodiments, the invention may also encompass cancer peptide vaccines that incorporate SEMA4D peptides in a pharmaceutical composition or as a fusion protein to stimulate a strong and effective antibody and/or cellular immune responses to SEMA4D. Specifically, the invention may encompass peptide vaccines comprised of at least one of, and in some embodiments, all of, the following sequences: SEQ ID NO:18 at the amino acid residue positions corresponding to positions 304 through 320 of SEQ ID NO:1, 14 or 16; SEQ ID NO:20 at the amino acid residue positions corresponding to positions 270 through 284 of SEQ ID NO:1, 14 or 16, wherein the cysteine at position 281 is replaced with alanine, and SEQ ID NO:22 at the amino acid residue positions corresponding to positions 243 through 256 of SEQ ID NO:1, 14 or 16. The present invention may also relate to pharmaceutical compositions containing the peptide vaccines. The vaccines may be used for the treatment of cancers which express target proteins, such as SEMA4D. These vaccines are likely to induce a strong, comprehensive immune response against the target proteins, and thereby induce an immune reaction against tumors expressing such target proteins.

All of the references cited above, as well as all references cited herein, are incorporated herein by reference in their entireties.

The following examples are offered by way of illustration and not by way of limitation.

EXAMPLES

Example 1

Method of Epitope Mapping

Epitope mapping was performed to identify the linear or non-linear, discontinuous amino acid sequence within an antigenic protein that is recognized by a particular monoclonal antibody. A general approach for epitope mapping requires the expression of the full-length protein, as well as various fragments (i.e., truncated forms, or peptides) of the protein, generally in a heterologous expression system (e.g., RTS System, "Rapid Translation System" Roche Applied Science). These various recombinant proteins and fragments thereof (e.g., fused with an N-terminal protein (e.g., GFP)) were then used to determine if the specific monoclonal antibody was capable of binding to one or more of the truncated forms of the target protein. Through the use of reiterative truncation and the generation of recombinant peptides with overlapping amino acid regions, it was possible to identify the region of the target protein (e.g., SEMA4D) that was recognized by the monoclonal antibody under investigation (VX15/2503). Western blot analysis, ELISA, or immunoprecipitation was employed to determine if the specific monoclonal antibody under investigation is capable of binding one or more of the recombinant protein fragments. This approach was ultimately used to identify the peptide regions that contained the epitope(s) and, in some cases, to refine the epitope(s) precisely to an approximately 5-15 amino acid sequence. An epitope can be a continuous linear sequence approximately 5-15 amino acids in length, nonlinear (e.g., discontinuous with the antibody binding to a site on the protein composed of different sections of the peptide chain), or both linear and nonlinear.

Example 2

Characterization of the Epitopes of VX15/2503 Antibodies

Epitope mapping for anti-SEMA4D antibody VX15/2503 was carried out essentially via the iterative process described above unless indicated otherwise. Further mapping was performed using CLIPS™ (Chemical Linkage of Immunogenic Peptides on Scaffolds) technology (available from Pepscan Presto) to map the conformational epitopes, where various peptides were chemically linked in order to produce synthetic scaffold peptides that mimic complex protein structures (e.g., secondary and tertiary structures) and juxtapose non-adjacent regions of the polypeptide to reconstruct the discontinuous epitope. (Meloen et al. (1997) Epitope mapping by PEPSCAN. In: Immunology Methods Manual, Ed. Ivan Lefkovits, Academic Press, pp 982-988). These synthetic scaffold peptides were analyzed by immunoassays for binding to the VX15/2503 monoclonal antibody. Alanine-scanning mutagenesis of the regions highlighted by the CLIPS™ analysis, in combination with immunoassays to measure the effects of the mutations on antibody binding, allowed for the identification of those residues that were important for the recognition by the anti-SEMA4D antibody VX15/2503.

Initial studies using the iterative process described above identified the epitope of the monoclonal antibody designated as VX15/2503 as LKVPVFYALFTPQLNNV (SEQ ID NO: 18, corresponding to residues 304 through 320 of the full-length SEMA4D amino acid sequence set forth in SEQ ID NO:1), KWTSFLKARLIASRP (SEQ ID NO: 20, corresponding to residues 270 through 284 of the full-length SEMA4D amino acid sequence set forth in SEQ ID NO:1, wherein the cysteine at position 281 was replaced with alanine during synthesis of the peptide), and EFVFRVLIPRIARV (SEQ ID NO:22; corresponding to residues 243 through 256 of the full-length SEMA4D amino acid sequence set forth in SEQ ID NO:1). The CLIPS™ analysis and alanine-scanning mutagenesis indicated that the most important sequence needed for binding of the VX15/2503 antibody to SEMA4D was the EFVFRVLIPRIARV sequence (SEQ ID NO:22).

The binding region in SEMA4D for the anti-SEMA4D antibody VX15/2503 was determined to be a conformational epitope. These three sequences were all part of the SEMA domain of the protein. More specifically, when analyzed in conjunction with the crystal structure of SEMA4D (Love, C A et al., "The ligand-binding face of the semaphorins revealed by the high-resolution crystal structure of SEMA4D." *Nature Structural Biology*, 10, 843-848, 2003), these three sequences were all located within one larger region that can form one discontinuous epitope on SEMA4D (e.g., residues 243 through 320 of SEQ ID NO:1).

Analysis of the binding region in SEMA4D for the anti-SEMA4D antibody VX15/2503 provided insight into the mechanism by which the VX15/2503 antibody interacts with SEMA4D. For instance, analysis revealed that the three epitope sequences were located within the homodimerization site of SEMA4D. Since homodimerization is known to be important in Semaphorin-Plexin signaling, binding of VX15/2503 antibody to this site suggests that VX15/2503 may interfere with homodimerization as a potential mechanism to block SEMA4D signaling. Furthermore, the epitope sequences were also located at the border of the binding interface of SEMA4D and its ligand, Plexin-B1 (Janssen, B J C et al. "Structural basis of semaphorin-plexin signalling." *Nature*, 467, 1118-1122, 2010), suggesting that VX15/2503 may hinder binding of SEMA4D to its receptor, Plexin-B1.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims and list of embodiments disclosed herein. Although specific terms are employed herein, they are used in a generic and descriptive sense only and not for purposes of limitation.

What is claimed is:

1. An isolated synthetic scaffold peptide polypeptide comprising (i) a SEMA4D conformational epitope formed by the three amino acid sequences set forth in SEQ ID NO:18, 20, and 22; and (ii) chemical linkers that join the amino acid sequences, wherein an anti-SEMA4D antibody binds the SEMA4D epitope polypeptide.

2. The synthetic scaffold peptide of claim 1, wherein the anti-SEMA4D antibody is MAb 2503 or an antigen-binding fragment thereof.

3. A peptide vaccine comprising the synthetic scaffold peptide of claim 1, wherein the peptide stimulates an antibody and/or cellular immune responses to SEMA4D.

4. The peptide vaccine of claim 3, consisting essentially of: (i) the amino acid sequences of SEQ ID NO:18, 20 and 22; and (ii)) the chemical linkers.

5. The synthetic scaffold polypeptide of claim 1, consisting essentially of: (i) the amino acid sequences set forth in SEQ ID NO: 18, 20 and 22; and (ii) the chemical linkers.

6. An isolated synthetic scaffold peptide that mimics a SEMA4D epitope that can be bound by MAb 2503, comprising at least two of the three amino acid sequences set forth in SEQ ID NO: 18, 20, and 22, wherein the amino acid sequences are chemically linked via a CLIPS™ (Chemical Linkage of Immunogenic Peptides on Scaffolds) scaffold.

7. The isolated synthetic scaffold peptide of claim 6, wherein the synthetic scaffold peptide comprises the three amino acid sequences set forth in SEQ ID NO: 18, 20, and 22.

* * * * *

SEQUENCE LISTING

```
<160> NUMBER OF SEQ ID NOS: 22

<210> SEQ ID NO 1
<211> LENGTH: 862
<212> TYPE: PRT
<213> ORGANISM: Homo sapiens

<400> SEQUENCE: 1

Met Arg Met Cys Thr Pro Ile Arg Gly Leu Leu Met Ala Leu Ala Val
1               5                   10                  15

Met Phe Gly Thr Ala Met Ala Phe Ala Pro Ile Pro Arg Ile Thr Trp
            20                  25                  30

Glu His Arg Glu Val His Leu Val Gln Phe His Glu Pro Asp Ile Tyr
        35                  40                  45

Asn Tyr Ser Ala Leu Leu Leu Ser Glu Asp Lys Asp Thr Leu Tyr Ile
    50                  55                  60

Gly Ala Arg Glu Ala Val Phe Ala Val Asn Ala Leu Asn Ile Ser Glu
65                  70                  75                  80

Lys Gln His Glu Val Tyr Trp Lys Val Ser Glu Asp Lys Lys Ala Lys
                85                  90                  95

Cys Ala Glu Lys Gly Lys Ser Lys Gln Thr Glu Cys Leu Asn Tyr Ile
            100                 105                 110

Arg Val Leu Gln Pro Leu Ser Ala Thr Ser Leu Tyr Val Cys Gly Thr
        115                 120                 125

Asn Ala Phe Gln Pro Ala Cys Asp His Leu Asn Leu Thr Ser Phe Lys
    130                 135                 140

Phe Leu Gly Lys Asn Glu Asp Gly Lys Gly Arg Cys Pro Phe Asp Pro
145                 150                 155                 160
```

```
Ala His Ser Tyr Thr Ser Val Met Val Asp Gly Glu Leu Tyr Ser Gly
                165                 170                 175

Thr Ser Tyr Asn Phe Leu Gly Ser Glu Pro Ile Ile Ser Arg Asn Ser
            180                 185                 190

Ser His Ser Pro Leu Arg Thr Glu Tyr Ala Ile Pro Trp Leu Asn Glu
        195                 200                 205

Pro Ser Phe Val Phe Ala Asp Val Ile Arg Lys Ser Pro Asp Ser Pro
    210                 215                 220

Asp Gly Glu Asp Asp Arg Val Tyr Phe Phe Thr Glu Val Ser Val
225                 230                 235                 240

Glu Tyr Glu Phe Val Phe Arg Val Leu Ile Pro Arg Ile Ala Arg Val
                245                 250                 255

Cys Lys Gly Asp Gln Gly Gly Leu Arg Thr Leu Gln Lys Lys Trp Thr
            260                 265                 270

Ser Phe Leu Lys Ala Arg Leu Ile Cys Ser Arg Pro Asp Ser Gly Leu
        275                 280                 285

Val Phe Asn Val Leu Arg Asp Val Phe Val Leu Arg Ser Pro Gly Leu
    290                 295                 300

Lys Val Pro Val Phe Tyr Ala Leu Phe Thr Pro Gln Leu Asn Asn Val
305                 310                 315                 320

Gly Leu Ser Ala Val Cys Ala Tyr Asn Leu Ser Thr Ala Glu Glu Val
                325                 330                 335

Phe Ser His Gly Lys Tyr Met Gln Ser Thr Val Glu Gln Ser His
            340                 345                 350

Thr Lys Trp Val Arg Tyr Asn Gly Pro Val Pro Lys Pro Arg Pro Gly
        355                 360                 365

Ala Cys Ile Asp Ser Glu Ala Arg Ala Ala Asn Tyr Thr Ser Ser Leu
    370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Arg Leu Ile Lys Lys
                405                 410                 415

Asp Val Asn Tyr Thr Gln Ile Val Val Asp Arg Thr Gln Ala Leu Asp
            420                 425                 430

Gly Thr Val Tyr Asp Val Met Phe Val Ser Thr Asp Arg Gly Ala Leu
        435                 440                 445

His Lys Ala Ile Ser Leu Glu His Ala Val His Ile Ile Glu Glu Thr
    450                 455                 460

Gln Leu Phe Gln Asp Phe Glu Pro Val Gln Thr Leu Leu Leu Ser Ser
465                 470                 475                 480

Lys Lys Gly Asn Arg Phe Val Tyr Ala Gly Ser Asn Ser Gly Val Val
                485                 490                 495

Gln Ala Pro Leu Ala Phe Cys Gly Lys His Gly Thr Cys Glu Asp Cys
            500                 505                 510

Val Leu Ala Arg Asp Pro Tyr Cys Ala Trp Ser Pro Pro Thr Ala Thr
        515                 520                 525

Cys Val Ala Leu His Gln Thr Glu Ser Pro Ser Arg Gly Leu Ile Gln
    530                 535                 540

Glu Met Ser Gly Asp Ala Ser Val Cys Pro Asp Lys Ser Lys Gly Ser
545                 550                 555                 560

Tyr Arg Gln His Phe Phe Lys His Gly Gly Thr Ala Glu Leu Lys Cys
                565                 570                 575
```

```
Ser Gln Lys Ser Asn Leu Ala Arg Val Phe Trp Lys Phe Gln Asn Gly
            580                 585                 590

Val Leu Lys Ala Glu Ser Pro Lys Tyr Gly Leu Met Gly Arg Lys Asn
            595                 600                 605

Leu Leu Ile Phe Asn Leu Ser Glu Gly Asp Ser Gly Val Tyr Gln Cys
            610                 615                 620

Leu Ser Glu Glu Arg Val Lys Asn Lys Thr Val Phe Gln Val Val Ala
625                 630                 635                 640

Lys His Val Leu Glu Val Lys Val Val Pro Lys Pro Val Val Ala Pro
                645                 650                 655

Thr Leu Ser Val Val Gln Thr Glu Gly Ser Arg Ile Ala Thr Lys Val
            660                 665                 670

Leu Val Ala Ser Thr Gln Gly Ser Ser Pro Pro Thr Pro Ala Val Gln
            675                 680                 685

Ala Thr Ser Ser Gly Ala Ile Thr Leu Pro Pro Lys Pro Ala Pro Thr
            690                 695                 700

Gly Thr Ser Cys Glu Pro Lys Ile Val Ile Asn Thr Val Pro Gln Leu
705                 710                 715                 720

His Ser Glu Lys Thr Met Tyr Leu Lys Ser Ser Asp Asn Arg Leu Leu
                725                 730                 735

Met Ser Leu Phe Leu Phe Phe Val Leu Phe Leu Cys Leu Phe
            740                 745                 750

Tyr Asn Cys Tyr Lys Gly Tyr Leu Pro Arg Gln Cys Leu Lys Phe Arg
                755                 760                 765

Ser Ala Leu Leu Ile Gly Lys Lys Pro Lys Ser Asp Phe Cys Asp
            770                 775                 780

Arg Glu Gln Ser Leu Lys Glu Thr Leu Val Glu Pro Gly Ser Phe Ser
785                 790                 795                 800

Gln Gln Asn Gly Glu His Pro Lys Pro Ala Leu Asp Thr Gly Tyr Glu
                805                 810                 815

Thr Glu Gln Asp Thr Ile Thr Ser Lys Val Pro Thr Arg Glu Asp
            820                 825                 830

Ser Gln Arg Ile Asp Asp Leu Ser Ala Arg Asp Lys Pro Phe Asp Val
            835                 840                 845

Lys Cys Glu Leu Lys Phe Ala Asp Ser Asp Ala Asp Gly Asp
            850                 855                 860

<210> SEQ ID NO 2
<211> LENGTH: 861
<212> TYPE: PRT
<213> ORGANISM: Murine sp.

<400> SEQUENCE: 2

Met Arg Met Cys Ala Pro Val Arg Gly Leu Phe Leu Ala Leu Val Val
1               5                   10                  15

Val Leu Arg Thr Ala Val Ala Phe Ala Pro Val Pro Arg Leu Thr Trp
            20                  25                  30

Glu His Gly Glu Val Gly Leu Val Gln Phe His Lys Pro Gly Ile Phe
        35                  40                  45

Asn Tyr Ser Ala Leu Leu Met Ser Glu Asp Lys Asp Thr Leu Tyr Val
    50                  55                  60

Gly Ala Arg Glu Ala Val Phe Ala Val Asn Ala Leu Asn Ile Ser Glu
65                  70                  75                  80

Lys Gln His Glu Val Tyr Trp Lys Val Ser Glu Asp Lys Lys Ser Lys
                85                  90                  95
```

```
Cys Ala Glu Lys Gly Lys Ser Lys Gln Thr Glu Cys Leu Asn Tyr Ile
            100                 105                 110

Arg Val Leu Gln Pro Leu Ser Thr Ser Leu Tyr Val Cys Gly Thr
            115                 120                 125

Asn Ala Phe Gln Pro Thr Cys Asp His Leu Asn Leu Thr Ser Phe Lys
            130                 135                 140

Phe Leu Gly Lys Ser Glu Asp Gly Lys Gly Arg Cys Pro Phe Asp Pro
145                 150                 155                 160

Ala His Ser Tyr Thr Ser Val Met Val Gly Gly Glu Leu Tyr Ser Gly
                165                 170                 175

Thr Ser Tyr Asn Phe Leu Gly Ser Glu Pro Ile Ile Ser Arg Asn Ser
            180                 185                 190

Ser His Ser Pro Leu Arg Thr Glu Tyr Ala Ile Pro Trp Leu Asn Glu
            195                 200                 205

Pro Ser Phe Val Phe Ala Asp Val Ile Gln Lys Ser Pro Asp Gly Pro
            210                 215                 220

Glu Gly Glu Asp Asp Lys Val Tyr Phe Phe Thr Glu Val Ser Val
225                 230                 235                 240

Glu Tyr Glu Phe Val Phe Lys Leu Met Ile Pro Arg Val Ala Arg Val
                245                 250                 255

Cys Lys Gly Asp Gln Gly Gly Leu Arg Thr Leu Gln Lys Lys Trp Thr
            260                 265                 270

Ser Phe Leu Lys Ala Arg Leu Ile Cys Ser Lys Pro Asp Ser Gly Leu
            275                 280                 285

Val Phe Asn Ile Leu Gln Asp Val Phe Val Leu Arg Ala Pro Gly Leu
            290                 295                 300

Lys Glu Pro Val Phe Tyr Ala Val Phe Thr Pro Gln Leu Asn Asn Val
305                 310                 315                 320

Gly Leu Ser Ala Val Cys Ala Tyr Thr Leu Ala Thr Val Glu Ala Val
                325                 330                 335

Phe Ser Arg Gly Lys Tyr Met Gln Ser Ala Thr Val Glu Gln Ser His
            340                 345                 350

Thr Lys Trp Val Arg Tyr Asn Gly Pro Val Pro Thr Pro Arg Pro Gly
            355                 360                 365

Ala Cys Ile Asp Ser Glu Ala Arg Ala Ala Asn Tyr Thr Ser Ser Leu
            370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Lys Leu Ile Lys Lys
                405                 410                 415

Asp Val Asn Tyr Thr Gln Ile Val Val Asp Arg Thr Gln Ala Leu Asp
            420                 425                 430

Gly Thr Phe Tyr Asp Val Met Phe Ile Ser Thr Asp Arg Gly Ala Leu
            435                 440                 445

His Lys Ala Val Ile Leu Thr Lys Glu Val His Val Ile Glu Glu Thr
            450                 455                 460

Gln Leu Phe Arg Asp Ser Glu Pro Val Leu Thr Leu Leu Ser Ser
465                 470                 475                 480

Lys Lys Gly Arg Lys Phe Val Tyr Ala Gly Ser Asn Ser Gly Val Val
                485                 490                 495

Gln Ala Pro Leu Ala Phe Cys Glu Lys His Gly Ser Cys Glu Asp Cys
            500                 505                 510
```

```
Val Leu Ala Arg Asp Pro Tyr Cys Ala Trp Ser Pro Ala Ile Lys Ala
            515                 520                 525

Cys Val Thr Leu His Gln Glu Glu Ala Ser Ser Arg Gly Trp Ile Gln
        530                 535                 540

Asp Met Ser Gly Asp Thr Ser Ser Cys Leu Asp Lys Ser Lys Glu Ser
545                 550                 555                 560

Phe Asn Gln His Phe Phe Lys His Gly Gly Thr Ala Glu Leu Lys Cys
                565                 570                 575

Phe Gln Lys Ser Asn Leu Ala Arg Val Val Trp Lys Phe Gln Asn Gly
            580                 585                 590

Glu Leu Lys Ala Ala Ser Pro Lys Tyr Gly Phe Val Gly Arg Lys His
        595                 600                 605

Leu Leu Ile Phe Asn Leu Ser Asp Gly Asp Ser Gly Val Tyr Gln Cys
    610                 615                 620

Leu Ser Glu Glu Arg Val Arg Asn Lys Thr Val Ser Gln Leu Leu Ala
625                 630                 635                 640

Lys His Val Leu Glu Val Lys Met Val Pro Arg Thr Pro Pro Ser Pro
                645                 650                 655

Thr Ser Glu Asp Ala Gln Thr Glu Gly Ser Lys Ile Thr Ser Lys Met
            660                 665                 670

Pro Val Ala Ser Thr Gln Gly Ser Ser Pro Pro Thr Pro Ala Leu Trp
        675                 680                 685

Ala Thr Ser Pro Arg Ala Ala Thr Leu Pro Pro Lys Ser Ser Ser Gly
    690                 695                 700

Thr Ser Cys Glu Pro Lys Met Val Ile Asn Thr Val Pro Gln Leu His
705                 710                 715                 720

Ser Glu Lys Thr Val Tyr Leu Lys Ser Ser Asp Asn Arg Leu Leu Met
                725                 730                 735

Ser Leu Leu Leu Phe Ile Phe Val Leu Phe Leu Cys Leu Phe Ser Tyr
            740                 745                 750

Asn Cys Tyr Lys Gly Tyr Leu Pro Gly Gln Cys Leu Lys Phe Arg Ser
        755                 760                 765

Ala Leu Leu Leu Gly Lys Lys Thr Pro Lys Ser Asp Phe Ser Asp Leu
    770                 775                 780

Glu Gln Ser Val Lys Glu Thr Leu Val Glu Pro Gly Ser Phe Ser Gln
785                 790                 795                 800

Gln Asn Gly Asp His Pro Lys Pro Ala Leu Asp Thr Gly Tyr Glu Thr
                805                 810                 815

Glu Gln Asp Thr Ile Thr Ser Lys Val Pro Thr Asp Arg Glu Asp Ser
            820                 825                 830

Gln Arg Ile Asp Glu Leu Ser Ala Arg Asp Lys Pro Phe Asp Val Lys
        835                 840                 845

Cys Glu Leu Lys Phe Ala Asp Ser Asp Ala Asp Gly Asp
    850                 855                 860

<210> SEQ ID NO 3
<211> LENGTH: 118
<212> TYPE: PRT
<213> ORGANISM: Artificial
<220> FEATURE:
<223> OTHER INFORMATION: Polypeptide anti-CD100 VH 2503

<400> SEQUENCE: 3

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Tyr Ser Phe Ser Asp Tyr
            20                  25                  30

Tyr Met His Trp Val Arg Gln Ala Pro Gly Gln Gly Leu Glu Trp Met
        35                  40                  45

Gly Gln Ile Asn Pro Thr Thr Gly Gly Ala Ser Tyr Asn Gln Lys Phe
    50                  55                  60

Lys Gly Lys Ala Thr Ile Thr Val Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Tyr Gly Arg His Phe Asp Val Trp Gly Gln Gly Thr
            100                 105                 110

Thr Val Thr Val Ser Ser
            115

<210> SEQ ID NO 4
<211> LENGTH: 118
<212> TYPE: PRT
<213> ORGANISM: Artificial
<220> FEATURE:
<223> OTHER INFORMATION: Polypeptide anti-CD100 VH 67

<400> SEQUENCE: 4

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Ser Asp Tyr
            20                  25                  30

Tyr Met His Trp Val Lys Gln Ser Pro Glu Asn Ser Leu Glu Trp Ile
        35                  40                  45

Gly Gln Ile Asn Pro Thr Thr Gly Gly Ala Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Glu Ser Ala Val Tyr Tyr Cys
                85                  90                  95

Thr Arg Tyr Tyr Tyr Gly Arg His Phe Asp Val Trp Gly Gln Gly Thr
            100                 105                 110

Thr Val Thr Val Ser Ser
            115

<210> SEQ ID NO 5
<211> LENGTH: 10
<212> TYPE: PRT
<213> ORGANISM: Artificial
<220> FEATURE:
<223> OTHER INFORMATION: Polypeptide anti-CD100 VH CDR1

<400> SEQUENCE: 5

Gly Tyr Ser Phe Ser Asp Tyr Tyr Met His
1               5                   10

<210> SEQ ID NO 6
<211> LENGTH: 17
<212> TYPE: PRT
<213> ORGANISM: Artificial
<220> FEATURE:
<223> OTHER INFORMATION: Polypeptide anti-CD100 VH CDR2

<400> SEQUENCE: 6

Gln Ile Asn Pro Thr Thr Gly Gly Ala Ser Tyr Asn Gln Lys Phe Lys
```

```
<210> SEQ ID NO 7
<211> LENGTH: 9
<212> TYPE: PRT
<213> ORGANISM: Artificial
<220> FEATURE:
<223> OTHER INFORMATION: Polypeptide anti-CD100 VH CDR3

<400> SEQUENCE: 7

Tyr Tyr Tyr Gly Arg His Phe Asp Val
1               5

<210> SEQ ID NO 8
<211> LENGTH: 111
<212> TYPE: PRT
<213> ORGANISM: Artificial
<220> FEATURE:
<223> OTHER INFORMATION: Polypeptide anti-CD100 VL 2503

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys
            100                 105                 110

<210> SEQ ID NO 9
<211> LENGTH: 111
<212> TYPE: PRT
<213> ORGANISM: Artificial
<220> FEATURE:
<223> OTHER INFORMATION: Polypeptide anti-CD100 VL 67

<400> SEQUENCE: 9

Asp Ile Val Met Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110
```

<210> SEQ ID NO 10
<211> LENGTH: 15
<212> TYPE: PRT
<213> ORGANISM: Artificial
<220> FEATURE:
<223> OTHER INFORMATION: Polypeptide anti-CD100 VL CDR1

<400> SEQUENCE: 10

Lys Ala Ser Gln Ser Val Asp Tyr Asp Gly Asp Ser Tyr Met Asn
1               5                   10                  15

<210> SEQ ID NO 11
<211> LENGTH: 7
<212> TYPE: PRT
<213> ORGANISM: Artificial
<220> FEATURE:
<223> OTHER INFORMATION: Polypeptide anti-CD100 VL CDR2

<400> SEQUENCE: 11

Ala Ala Ser Asn Leu Glu Ser
1               5

<210> SEQ ID NO 12
<211> LENGTH: 9
<212> TYPE: PRT
<213> ORGANISM: Artificial
<220> FEATURE:
<223> OTHER INFORMATION: Polypeptide anti-CD100 VL CDR3

<400> SEQUENCE: 12

Gln Gln Ser Asn Glu Asp Pro Tyr Thr
1               5

<210> SEQ ID NO 13
<211> LENGTH: 4630
<212> TYPE: DNA
<213> ORGANISM: Artificial
<220> FEATURE:
<223> OTHER INFORMATION: SEMA4D Variant 1

<400> SEQUENCE: 13

```
gctgtaacac tcaccgtgaa ggtctgcagc ttcactcccg agccagcgag accacgaacc      60
caccagaagg aagaaactct gaacacatct gaacatcaga agggacagac tccagacgcg     120
ccaccactct gctaacacca gatagtggaa agaaaccatg tgctgaaatg tttgacgaca     180
ctgatggttt gactctgcta actggaatgg cttattgtgc aagaaagtac acctggtcgg     240
gtcctggggc tcatctctag caccagcaaa gatttctgaa gacgtctttc tagaaatgac     300
tggaaagttt caagaggcat aagatacagc atttcttctg aggccctgaa gaagtatcaa     360
gtgggctttg acattgcggt ggtgagagcg accccctcct acctggagaa ctgggaaatg     420
tggattctca gggaccgcgc tgttcacgag ctccaggctg tgctgctggc cctggtcctg     480
gggcgctgag ccgcatctgc aatagcacac ttgcccggcc acctgctgcc gtgagccttt     540
gctgctgaag cccctggggt cgcctctacc tgatgaggat gtgcaccccc attaggggc      600 tgctcatggc ccttgcagtg atgtttggga cagcgatggc atttgcaccc ataccccgga     660
tcacctggga gcacagagag gtgcacctgg tgcagtttca tgagccagac atctacaact     720
actcagcctt gctgctgagc gaggacaagg acaccttgta cataggtgcc cggaggcgg      780 tcttcgctgt gaacgcactc aacatctccg agaagcagca tgaggtgtat tggaaggtct     840
cagaagacaa aaaagcaaaa tgtgcagaaa aggggaaatc aaaacagaca gagtgcctca     900
```

| | |
|---|---|
| actacatccg ggtgctgcag ccactcagcg ccacttccct ttacgtgtgt gggaccaacg | 960 |
| cattccagcc ggcctgtgac cacctgaact taacatcctt taagtttctg gggaaaaatg | 1020 |
| aagatggcaa aggaagatgt ccctttgacc cagcacacag ctacacatcc gtcatggttg | 1080 |
| atggagaact ttattcgggg acgtcgtata attttttggg aagtgaaccc atcatctccc | 1140 |
| gaaattcttc ccacagtcct ctgaggacag aatatgcaat cccttggctg aacgagccta | 1200 |
| gtttcgtgtt tgctgacgtg atccgaaaaa gcccagacag ccccgacggc gaggatgaca | 1260 |
| gggtctactt cttcttcacg gaggtgtctg tggagtatga gtttgtgttc agggtgctga | 1320 |
| tcccacggat agcaagagtg tgcaaggggg accagggcgg cctgaggacc ttgcagaaga | 1380 |
| aatggacctc cttcctgaaa gcccgactca tctgctcccg gccagacagc ggcttggtct | 1440 |
| tcaatgtgct gcgggatgtc ttcgtgctca ggtccccggg cctgaaggtg cctgtgttct | 1500 |
| atgcactctt caccccacag ctgaacaacg tggggctgtc ggcagtgtgc gcctacaacc | 1560 |
| tgtccacagc cgaggaggtc ttctcccacg ggaagtacat gcagagcacc acagtggagc | 1620 |
| agtcccacac caagtgggtg cgctataatg gcccggtacc caagccgcgg cctggagcgt | 1680 |
| gcatcgacag cgaggcacgg gccgccaact acaccagctc cttgaatttg ccagacaaga | 1740 |
| cgctgcagtt cgttaaagac cacccttga tggatgactg ggtaacccca atagacaaca | 1800 |
| ggcccaggtt aatcaagaaa gatgtgaact cacccagat cgtggtggac cggacccagg | 1860 |
| ccctggatgg gactgtctat gatgtcatgt ttgtcagcac agaccgggga gctctgcaca | 1920 |
| aagccatcag cctcgagcac gctgttcaca tcatcgagga acccagctc ttccaggact | 1980 |
| ttgagccagt ccagaccctg ctgctgtctt caaagaaggg caacaggttt gtctatgctg | 2040 |
| gctctaactc gggcgtggtc caggccccgc tggccttctg tgggaagcac ggcacctgcg | 2100 |
| aggactgtgt gctggcgcgg gaccctact gcgcctggag cccgcccaca gcgacctgcg | 2160 |
| tggctctgca ccagaccgag agcccagca ggggtttgat tcaggagatg agcggcgatg | 2220 |
| cttctgtgtg cccggataaa agtaaaggaa gttaccggca gcatttttc aagcacggtg | 2280 |
| gcacagcgga actgaaatgc tcccaaaaat ccaacctggc ccgggtctttt tggaagttcc | 2340 |
| agaatggcgt gttgaaggcc gagagcccca agtacggtct tatgggcaga aaaaacttgc | 2400 |
| tcatcttcaa cttgtcagaa ggagacagtg gggtgtacca gtgcctgtca gaggagaggg | 2460 |
| ttaagaacaa aacggtcttc caagtggtcg ccaagcacgt cctggaagtg aaggtggttc | 2520 |
| caaagcccgt agtggccccc accttgtcag ttgttcagac agaaggtagt aggattgcca | 2580 |
| ccaaagtgtt ggtggcatcc acccaagggt cttctccccc aaccccagcc gtgcaggcca | 2640 |
| cctcctccgg ggccatcacc cttcctccca agcctgcgcc caccggcaca tcctgcgaac | 2700 |
| caaagatcgt catcaacacg gtcccccagc tccactcgga gaaaccatg tatcttaagt | 2760 |
| ccagcgacaa ccgcctcctc atgtccctct tcctcttctt ctttgttctc ttcctctgcc | 2820 |
| tcttttctta caactgctat aagggatacc tgcccagaca gtgcttgaaa ttccgctcgg | 2880 |
| ccctactaat tgggaagaag aagcccaagt cagatttctg tgaccgtgag cagagcctga | 2940 |
| aggagacgtt agtagagcca gggagcttct cccagcagaa tgggagcac cccaagccag | 3000 |
| ccctggacac cggctatgag accgagcaag acaccatcac cagcaaagtc cccacggata | 3060 |
| gggaggactc acagaggatc gacgaccttt ctgccaggga caagcccttt gacgtcaagt | 3120 |
| gtgagctgaa gttcgctgac tcagacgcag atggagactg aggccggctg tgcatcccg | 3180 |
| ctggtgcctc ggctgcgacg tgtccaggcg tggagagttt tgtgtttctc ctgttcagta | 3240 |
| tccgagtctc gtgcagtgct gcgtaggtta gcccgcatcg tgcagacaac ctcagtcctc | 3300 |

```
ttgtctattt tctcttgggt tgagcctgtg acttggtttc tctttgtcct tttggaaaaa    3360
tgacaagcat tgcatcccag tcttgtgttc cgaagtcagt cggagtactt gaagaaggcc    3420
cacgggcggc acggagttcc tgagcccttt ctgtagtggg ggaaaggtgg ctggacctct    3480
gttggctgag aagagcatcc cttcagcttc ccctccccgt agcagccact aaaagattat    3540
ttaattccag attggaaatg acattttagt ttatcagatt ggtaacttat cgcctgttgt    3600
ccagattggc acgaaccttt tcttccactt aattattttt ttaggatttt gctttgattg    3660
tgtttatgtc atgggtcatt ttttttagt tacagaagca gttgtgttaa tatttagaag    3720
aagatgtata tcttccagat tttgttatat atttggcata aaatacggct tacgttgctt    3780
aagattctca gggataaact tccttttgct aaatgcattc tttctgcttt tagaaatgta    3840
gacataaaca ctccccggag cccactcacc tttttctttt tctttttttt tttttaact    3900 ttattccttg agggaagcat tgttttggaa gagattttct ttctgtactt cgttttactt    3960 ttctttttt taacttttta ctctctcgaa gaagaggacc ttcccacatc acgaggtgg     4020 gttttgagca agggaaggta gcctggatga gctgagtgga gccaggctgg cccagagctg    4080
agatgggagt gcggtacaat ctggagccca cagctgtcgg tcagaacctc ctgtgagaca    4140
gatggaacct tcacaagggc gcctttggtt ctctgaacat ctcctttctc ttcttgcttc    4200
aattgcttac ccactgcctg cccagacttt ctatccagcc tcactgagct gcccactact    4260
ggaagggaac tgggcctcgg tggccgggc cgcgagctgt gaccacagca ccctcaagca     4320
tacggcgctg ttcctgccac tgtcctgaag atgtgaatgg gtggtacgat ttcaacactg    4380
gttaatttca cactccatct ccccgctttg taaataccca tcgggaagag acttttttttc   4440 catggtgaag agcaataaac tctgatgtt tgtgcgcgtg tgtggacagt cttatcttcc     4500
agcatgatag gatttgacca ttttggtgta aacatttgtg tttataaga tttaccttgt     4560 ttttattttt ctactttgaa ttgtatacat ttggaaagta cccaaataaa tgagaagctt    4620
ctatccttaa                                                           4630
```

<210> SEQ ID NO 14
<211> LENGTH: 862
<212> TYPE: PRT
<213> ORGANISM: Artificial
<220> FEATURE:
<223> OTHER INFORMATION: SEMA4D Variant 1

<400> SEQUENCE: 14

```
Met Arg Met Cys Thr Pro Ile Arg Gly Leu Leu Met Ala Leu Ala Val
1               5                   10                  15

Met Phe Gly Thr Ala Met Ala Phe Ala Pro Ile Pro Arg Ile Thr Trp
            20                  25                  30

Glu His Arg Glu Val His Leu Val Gln Phe His Glu Pro Asp Ile Tyr
        35                  40                  45

Asn Tyr Ser Ala Leu Leu Leu Ser Glu Asp Lys Asp Thr Leu Tyr Ile
    50                  55                  60

Gly Ala Arg Glu Ala Val Phe Ala Val Asn Ala Leu Asn Ile Ser Glu
65                  70                  75                  80

Lys Gln His Glu Val Tyr Trp Lys Val Ser Glu Asp Lys Lys Ala Lys
                85                  90                  95

Cys Ala Glu Lys Gly Lys Ser Lys Gln Thr Glu Cys Leu Asn Tyr Ile
            100                 105                 110

Arg Val Leu Gln Pro Leu Ser Ala Thr Ser Leu Tyr Val Cys Gly Thr
```

```
                115                 120                 125
Asn Ala Phe Gln Pro Ala Cys Asp His Leu Asn Leu Thr Ser Phe Lys
130                 135                 140

Phe Leu Gly Lys Asn Glu Asp Gly Lys Gly Arg Cys Pro Phe Asp Pro
145                 150                 155                 160

Ala His Ser Tyr Thr Ser Val Met Val Asp Gly Glu Leu Tyr Ser Gly
                165                 170                 175

Thr Ser Tyr Asn Phe Leu Gly Ser Glu Pro Ile Ile Ser Arg Asn Ser
                180                 185                 190

Ser His Ser Pro Leu Arg Thr Glu Tyr Ala Ile Pro Trp Leu Asn Glu
            195                 200                 205

Pro Ser Phe Val Phe Ala Asp Val Ile Arg Lys Ser Pro Asp Ser Pro
210                 215                 220

Asp Gly Glu Asp Asp Arg Val Tyr Phe Phe Thr Glu Val Ser Val
225                 230                 235                 240

Glu Tyr Glu Phe Val Phe Arg Val Leu Ile Pro Arg Ile Ala Arg Val
                245                 250                 255

Cys Lys Gly Asp Gln Gly Gly Leu Arg Thr Leu Gln Lys Lys Trp Thr
            260                 265                 270

Ser Phe Leu Lys Ala Arg Leu Ile Cys Ser Arg Pro Asp Ser Gly Leu
    275                 280                 285

Val Phe Asn Val Leu Arg Asp Val Phe Val Leu Arg Ser Pro Gly Leu
290                 295                 300

Lys Val Pro Val Phe Tyr Ala Leu Phe Thr Pro Gln Leu Asn Asn Val
305                 310                 315                 320

Gly Leu Ser Ala Val Cys Ala Tyr Asn Leu Ser Thr Ala Glu Glu Val
                325                 330                 335

Phe Ser His Gly Lys Tyr Met Gln Ser Thr Thr Val Glu Gln Ser His
            340                 345                 350

Thr Lys Trp Val Arg Tyr Asn Gly Pro Val Pro Lys Pro Arg Pro Gly
    355                 360                 365

Ala Cys Ile Asp Ser Glu Ala Arg Ala Ala Asn Tyr Thr Ser Ser Leu
370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Arg Leu Ile Lys Lys
                405                 410                 415

Asp Val Asn Tyr Thr Gln Ile Val Val Asp Arg Thr Gln Ala Leu Asp
            420                 425                 430

Gly Thr Val Tyr Asp Val Met Phe Val Ser Thr Asp Arg Gly Ala Leu
    435                 440                 445

His Lys Ala Ile Ser Leu Glu His Ala Val His Ile Ile Glu Glu Thr
450                 455                 460

Gln Leu Phe Gln Asp Phe Glu Pro Val Gln Thr Leu Leu Ser Ser
465                 470                 475                 480

Lys Lys Gly Asn Arg Phe Val Tyr Ala Gly Ser Asn Ser Gly Val Val
                485                 490                 495

Gln Ala Pro Leu Ala Phe Cys Gly Lys His Gly Thr Cys Glu Asp Cys
            500                 505                 510

Val Leu Ala Arg Asp Pro Tyr Cys Ala Trp Ser Pro Pro Thr Ala Thr
    515                 520                 525

Cys Val Ala Leu His Gln Thr Glu Ser Pro Ser Arg Gly Leu Ile Gln
530                 535                 540
```

Glu Met Ser Gly Asp Ala Ser Val Cys Pro Asp Lys Ser Lys Gly Ser
545                 550                 555                 560

Tyr Arg Gln His Phe Lys His Gly Gly Thr Ala Glu Leu Lys Cys
            565                 570                 575

Ser Gln Lys Ser Asn Leu Ala Arg Val Phe Trp Lys Phe Gln Asn Gly
                580                 585                 590

Val Leu Lys Ala Glu Ser Pro Lys Tyr Gly Leu Met Gly Arg Lys Asn
            595                 600                 605

Leu Leu Ile Phe Asn Leu Ser Glu Gly Asp Ser Gly Val Tyr Gln Cys
        610                 615                 620

Leu Ser Glu Glu Arg Val Lys Asn Lys Thr Val Phe Gln Val Val Ala
625                 630                 635                 640

Lys His Val Leu Glu Val Lys Val Val Pro Lys Pro Val Val Ala Pro
                645                 650                 655

Thr Leu Ser Val Val Gln Thr Glu Gly Ser Arg Ile Ala Thr Lys Val
            660                 665                 670

Leu Val Ala Ser Thr Gln Gly Ser Ser Pro Pro Thr Pro Ala Val Gln
        675                 680                 685

Ala Thr Ser Ser Gly Ala Ile Thr Leu Pro Pro Lys Pro Ala Pro Thr
690                 695                 700

Gly Thr Ser Cys Glu Pro Lys Ile Val Ile Asn Thr Val Pro Gln Leu
705                 710                 715                 720

His Ser Glu Lys Thr Met Tyr Leu Lys Ser Ser Asp Asn Arg Leu Leu
                725                 730                 735

Met Ser Leu Phe Leu Phe Phe Val Leu Phe Leu Cys Leu Phe Phe
            740                 745                 750

Tyr Asn Cys Tyr Lys Gly Tyr Leu Pro Arg Gln Cys Leu Lys Phe Arg
        755                 760                 765

Ser Ala Leu Leu Ile Gly Lys Lys Pro Lys Ser Asp Phe Cys Asp
770                 775                 780

Arg Glu Gln Ser Leu Lys Glu Thr Leu Val Glu Pro Gly Ser Phe Ser
785                 790                 795                 800

Gln Gln Asn Gly Glu His Pro Lys Pro Ala Leu Asp Thr Gly Tyr Glu
                805                 810                 815

Thr Glu Gln Asp Thr Ile Thr Ser Lys Val Pro Thr Asp Arg Glu Asp
            820                 825                 830

Ser Gln Arg Ile Asp Asp Leu Ser Ala Arg Asp Lys Pro Phe Asp Val
        835                 840                 845

Lys Cys Glu Leu Lys Phe Ala Asp Ser Asp Ala Asp Gly Asp
850                 855                 860

<210> SEQ ID NO 15
<211> LENGTH: 4400
<212> TYPE: DNA
<213> ORGANISM: Artificial
<220> FEATURE:
<223> OTHER INFORMATION: SEMA4D Variant 2

<400> SEQUENCE: 15
gctgtaacac tcaccgtgaa ggtctgcagc ttcactcccg agccagcgag accacgaacc        60
caccagaagg aagaaactct gaacacatct gaacatcaga agggacagac tccagacgcg       120
ccaccactct gctaacacca gatagtggaa agaaaccatg tgctgaaatg tttgacgaca       180
ctgatggttt gactctgcta actggaatgg cttattgtgc aagaaagtac acctggtcgg       240

```
gtcctggggc tcatctctag caccagcaaa gatttctgaa gacgtctttc tagaaatgac    300
tggaaagttt caagaggcat aagatacagc atttcttctg aggccctgaa gaagtatcaa    360
gtgggctttg acattgcggt ggtgagagcg acccctcctc acctggagaa ctgggaaatg    420
tggattctca gggaccgcgc tgttcacgag ctccaggctg tgctgctggc cctggtcctg    480
gggcgctgag ccgcatctgc aatagcacac ttgcccggcc acctgctgcc gtgagccttt    540
gctgctgaag cccctggggt cgcctctacc tgatgaggat gtgcacccc attaggggc     600 tgctcatggc ccttgcagtg atgtttggga cagcgatggc atttgcaccc ataccccgga    660
tcacctggga gcacagagag gtgcacctgg tgcagtttca tgagccagac atctacaact    720
actcagcctt gctgctgagc gaggacaagg acaccttgta cataggtgcc cgggaggcgg    780
tcttcgctgt gaacgcactc aacatctccg agaagcagca tgaggtgtat tggaaggtct    840
cagaagacaa aaaagcaaaa tgtgcagaaa aggggaaatc aaaacagaca gagtgcctca    900
actacatccg ggtgctgcag ccactcagcg ccacttccct ttacgtgtgt gggaccaacg    960
cattccagcc ggcctgtgac cacctgaact taacatcctt taagtttctg gggaaaaatg   1020
aagatggcaa aggaagatgt ccctttgacc cagcacacag ctacacatcc gtcatggttg   1080
atggagaact ttattcgggg acgtcgtata atttttggg aagtgaaccc atcatctccc    1140
gaaattcttc ccacagtcct ctgaggacag aatatgcaat cccttggctg aacgagccta   1200
gtttcgtgtt tgctgacgtg atccgaaaaa gcccagacag ccccgacggc gaggatgaca   1260
gggtctactt cttcttcacg gaggtgtctg tggagtatga gtttgtgttc agggtgctga   1320
tcccacggat agcaagagtg tgcaaggggg accaggcgg cctgaggacc ttgcagaaga   1380
aatggaccct cttcctgaaa gcccgactca tctgctcccg gccagacagc ggcttggtct   1440
tcaatgtgct gcgggatgtc ttcgtgctca ggtccccggg cctgaaggtg cctgtgttct   1500
atgcactctt caccccacag ctgaacaacg tgggctgtc ggcagtgtgc gcctacaacc    1560
tgtccacagc cgaggaggtc ttctcccacg ggaagtacat gcagagcacc acagtggagc   1620
agtcccacac caagtgggtg cgctataatg gcccggtacc caagccgcgg cctggagcgt   1680
gcatcgacag cgaggcacgg gccgccaact acaccagctc cttgaatttg ccagacaaga   1740
cgctgcagtt cgttaaagac cacccttttga tggatgactc ggtaaccca atagacaaca   1800 ggcccaggtt aatcaagaaa gatgtgaact acacccagat cgtggtggac cggacccagg   1860
ccctggatgg gactgtctat gatgtcatgt tgtcagcac agaccgggga gctctgcaca   1920
aagccatcag cctcgagcac gctgttcaca tcatcgagga gacccagctc ttccaggact   1980
ttgagccagt ccagaccctg ctgctgtctt caaagaaggg caacaggttt gtctatgctg   2040
gctctaactc gggcgtggtc caggcccgc tggccttctg tgggaagcac ggcacctgcg    2100
aggactgtgt gctggcgcgg gacccctact gcgcctggag cccgcccaca gcgacctgcg   2160
tggctctgca ccagaccgag agccccagca ggggtttgat tcaggagatg agcggcgatg   2220
cttctgtgtg cccggcctcg tctcctaagc ccctccctcc tcctggctcc tcttccctgt   2280
cctgtctggg ccatgtgggg gacaggaggc tttcctctcc ctggacccc tggccagcct    2340 cgggtgcggg gcccgacagc agctcgaggg tctccttgct gccgcccttc ctgagtgacc   2400
aggcacagca cgtgcacgcc ctggggaact tctacctctt ctgccaggcc acaggtcctg   2460
cagacattcg ctttgtctgg gagaagaatg ggcgagctct ggagacctgt gtccctgtgc   2520
agacccatgc actgccgat ggcagggccc atgcactcag ctggctgcag gacgccatca   2580
gggaaagcgc tgagtatcgc tgctctgtcc tctcctcagc agggaacaag acttcgaagg   2640
```

-continued

```
tgcaggttgc tgtgatgaga cctgaagtga cccaccagga gaggtggacc agagagctct    2700
ctgcctggag ggctgtggct ggggagcacg accggatgat gcagagctgg aggaaggcgt    2760
gggaaagctg tagcaaggac accctgtagc caccaggaag gagtccctga caccgacctc    2820
aaccccaaca gaccctgctg ccactgacca cagccacccc cggagaaggg cctggtcccc    2880
cacaactgtg aactgtcttg cccaagcctg ctctgaacac agccattggg ccaccacctg    2940
atgggcagag gcgggacagt ggagaagcct ggaacccaag tgggcctgtg acaggaacta    3000
agacttaaaa aattaggtgc ttacctggga cagtaagttc tgtctggcac aagcaggtaa    3060
ccaggatggc taacaggctt tgatagctgc tcgtgaacta aaacagcagg gtgtgtgcag    3120
gttcctcctc tacggtcagg cagcaggctc tgaaggctga tcctacaccg tcccagtgac    3180 tcccctttgac agagtgcccc cacccccctaa tagccaacag ggttagcatg ccagcacag    3240 atcgctgctt ttattgatgc aaatcaagcc tgctgcttct cctccctgca gacttagcca    3300
aggaactcca agatgcatga ctgggacaag aaaaggtgag actccacatg gaaatgcctt    3360
gccctaaacc ttgaatgact gtgagatgcg atctgggagt gcatctgtca agtctttgtg    3420
ttttcttcac taacctcaga atactgggct ctatttttatc aagcgctgca gtttatgcct    3480
ctgtcccgtc aatgctcagc ttctgcaaca ggacaccaaa cttgatgcag aaagccaaat    3540
aggtcaatta tgcaaatctc ctggtgccat attaaatttc ttgacgatgg aatgagtctc    3600
atgagtgttt tgttctacct gctttcaagt ctctaattat taaagctgta tctctgaaga    3660
ctgtgtcact gtgtgtgtga acttgtccta aagctactca gcctttaatc ttacacacac    3720
gtctcttctt gtctgttgaa tgacagtttt catgtctatc ataaaaccaa agcctctgtt    3780
aaaagtcaag ccgcacccct ctggtgatcc tagcaaatac tgagtgtctt ccagcagtg    3840 tgacaatgac ctgttttgca tccctctttt ctggagctgg acaaattctc taccagcctt    3900
tgtgtgggat cagcatacat cgcctgctaa ttccttcagg atccatcaca acaggtgtcc    3960
tgaagatgct ggagacaccc tggttgtctc cacacgttcc ccctccgcac ccaagtcga    4020 gaggcccagc tgcctgtgag gtgtgtgctt gcccatccag ccaaggatgc cagtcttgct    4080
cacggaacca tcacatactc ataacctgaa gttttcctgt aaaatatcca tcagctcact    4140
gtggttcttg ctttgggtgt ggcttcaacc actacaaact gatgagtgaa atgctatggg    4200
ctttaggctt atattcttgg tgctgttttc tgtctcttct cctgaagtct ggatttcaag    4260
cactttcaca cttaacaaaa taattacata cttgaagttt tcgtaatgtg gagtgttcta    4320
ctgggaaatg gagttatgag gatgaatttc tgagtctttc tttgctctgc tggaaaaat    4380 aaaaatagag ttgtacattg                                                  4400
```

<210> SEQ ID NO 16
<211> LENGTH: 738
<212> TYPE: PRT
<213> ORGANISM: Artificial
<220> FEATURE:
<223> OTHER INFORMATION: SEMA4D Variant 2

<400> SEQUENCE: 16

Met Arg Met Cys Thr Pro Ile Arg Gly Leu Leu Met Ala Leu Ala Val
1               5                   10                  15

Met Phe Gly Thr Ala Met Ala Phe Ala Pro Ile Pro Arg Ile Thr Trp
            20                  25                  30

Glu His Arg Glu Val His Leu Val Gln Phe His Glu Pro Asp Ile Tyr
        35                  40                  45

```
Asn Tyr Ser Ala Leu Leu Ser Glu Asp Lys Asp Thr Leu Tyr Ile
        50                  55                  60

Gly Ala Arg Glu Ala Val Phe Ala Val Asn Ala Leu Asn Ile Ser Glu
65                  70                  75                  80

Lys Gln His Glu Val Tyr Trp Lys Val Ser Glu Asp Lys Lys Ala Lys
                    85                  90                  95

Cys Ala Glu Lys Gly Lys Ser Lys Gln Thr Glu Cys Leu Asn Tyr Ile
                100                 105                 110

Arg Val Leu Gln Pro Leu Ser Ala Thr Ser Leu Tyr Val Cys Gly Thr
            115                 120                 125

Asn Ala Phe Gln Pro Ala Cys Asp His Leu Asn Leu Thr Ser Phe Lys
        130                 135                 140

Phe Leu Gly Lys Asn Glu Asp Gly Lys Gly Arg Cys Pro Phe Asp Pro
145                 150                 155                 160

Ala His Ser Tyr Thr Ser Val Met Val Asp Gly Glu Leu Tyr Ser Gly
                    165                 170                 175

Thr Ser Tyr Asn Phe Leu Gly Ser Glu Pro Ile Ile Ser Arg Asn Ser
                180                 185                 190

Ser His Ser Pro Leu Arg Thr Glu Tyr Ala Ile Pro Trp Leu Asn Glu
            195                 200                 205

Pro Ser Phe Val Phe Ala Asp Val Ile Arg Lys Ser Pro Asp Ser Pro
        210                 215                 220

Asp Gly Glu Asp Asp Arg Val Tyr Phe Phe Phe Thr Glu Val Ser Val
225                 230                 235                 240

Glu Tyr Glu Phe Val Phe Arg Val Leu Ile Pro Arg Ile Ala Arg Val
                    245                 250                 255

Cys Lys Gly Asp Gln Gly Gly Leu Arg Thr Leu Gln Lys Lys Trp Thr
                260                 265                 270

Ser Phe Leu Lys Ala Arg Leu Ile Cys Ser Arg Pro Asp Ser Gly Leu
            275                 280                 285

Val Phe Asn Val Leu Arg Asp Val Phe Val Leu Arg Ser Pro Gly Leu
        290                 295                 300

Lys Val Pro Val Phe Tyr Ala Leu Phe Thr Pro Gln Leu Asn Asn Val
305                 310                 315                 320

Gly Leu Ser Ala Val Cys Ala Tyr Asn Leu Ser Thr Ala Glu Glu Val
                    325                 330                 335

Phe Ser His Gly Lys Tyr Met Gln Ser Thr Val Glu Gln Ser His
                340                 345                 350

Thr Lys Trp Val Arg Tyr Asn Gly Pro Val Pro Lys Pro Arg Pro Gly
            355                 360                 365

Ala Cys Ile Asp Ser Glu Ala Arg Ala Ala Asn Tyr Thr Ser Ser Leu
        370                 375                 380

Asn Leu Pro Asp Lys Thr Leu Gln Phe Val Lys Asp His Pro Leu Met
385                 390                 395                 400

Asp Asp Ser Val Thr Pro Ile Asp Asn Arg Pro Arg Leu Ile Lys Lys
                    405                 410                 415

Asp Val Asn Tyr Thr Gln Ile Val Val Asp Arg Thr Gln Ala Leu Asp
                420                 425                 430

Gly Thr Val Tyr Asp Val Met Phe Val Ser Thr Asp Arg Gly Ala Leu
            435                 440                 445

His Lys Ala Ile Ser Leu Glu His Ala Val His Ile Ile Glu Glu Thr
        450                 455                 460
```

```
Gln Leu Phe Gln Asp Phe Glu Pro Val Gln Thr Leu Leu Ser Ser
465                 470                 475                 480

Lys Lys Gly Asn Arg Phe Val Tyr Ala Gly Ser Asn Ser Gly Val Val
            485                 490                 495

Gln Ala Pro Leu Ala Phe Cys Gly Lys His Gly Thr Cys Glu Asp Cys
        500                 505                 510

Val Leu Ala Arg Asp Pro Tyr Cys Ala Trp Ser Pro Thr Ala Thr
        515                 520                 525

Cys Val Ala Leu His Gln Thr Glu Ser Pro Ser Arg Gly Leu Ile Gln
        530                 535                 540

Glu Met Ser Gly Asp Ala Ser Val Cys Pro Ala Ser Ser Pro Lys Pro
545                 550                 555                 560

Leu Pro Pro Pro Gly Ser Ser Leu Ser Cys Leu Gly His Val Gly
                565                 570                 575

Asp Arg Arg Leu Ser Ser Pro Trp Thr Pro Trp Pro Ala Ser Gly Ala
            580                 585                 590

Gly Pro Asp Ser Ser Ser Arg Val Ser Leu Leu Pro Pro Phe Leu Ser
            595                 600                 605

Asp Gln Ala Gln His Val His Ala Leu Gly Asn Phe Tyr Leu Phe Cys
610                 615                 620

Gln Ala Thr Gly Pro Ala Asp Ile Arg Phe Val Trp Glu Lys Asn Gly
625                 630                 635                 640

Arg Ala Leu Glu Thr Cys Val Pro Val Gln Thr His Ala Leu Pro Asp
                645                 650                 655

Gly Arg Ala His Ala Leu Ser Trp Leu Gln Asp Ala Ile Arg Glu Ser
            660                 665                 670

Ala Glu Tyr Arg Cys Ser Val Leu Ser Ser Ala Gly Asn Lys Thr Ser
            675                 680                 685

Lys Val Gln Val Ala Val Met Arg Pro Glu Val Thr His Gln Glu Arg
            690                 695                 700

Trp Thr Arg Glu Leu Ser Ala Trp Arg Ala Val Ala Gly Glu His Asp
705                 710                 715                 720

Arg Met Met Gln Ser Trp Arg Lys Ala Trp Glu Ser Cys Ser Lys Asp
                725                 730                 735

Thr Leu
```

```
<210> SEQ ID NO 17
<211> LENGTH: 51
<212> TYPE: DNA
<213> ORGANISM: Artificial
<220> FEATURE:
<223> OTHER INFORMATION: Epitope 1

<400> SEQUENCE: 17
ctgaaggtgc ctgtgttcta tgcactcttc accccacagc tgaacaacgt g          51

<210> SEQ ID NO 18
<211> LENGTH: 17
<212> TYPE: PRT
<213> ORGANISM: Artificial
<220> FEATURE:
<223> OTHER INFORMATION: Epitope 1

<400> SEQUENCE: 18

Leu Lys Val Pro Val Phe Tyr Ala Leu Phe Thr Pro Gln Leu Asn Asn
1               5                   10                  15

Val
```

-continued

```
<210> SEQ ID NO 19
<211> LENGTH: 45
<212> TYPE: DNA
<213> ORGANISM: Artificial
<220> FEATURE:
<223> OTHER INFORMATION: Epitope 2

<400> SEQUENCE: 19
aaatggacct ccttcctgaa agcccgactc atctgctccc ggcca                    45

<210> SEQ ID NO 20
<211> LENGTH: 15
<212> TYPE: PRT
<213> ORGANISM: Artificial
<220> FEATURE:
<223> OTHER INFORMATION: Epitope 2

<400> SEQUENCE: 20

Lys Trp Thr Ser Phe Leu Lys Ala Arg Leu Ile Ala Ser Arg Pro
1               5                   10                  15

<210> SEQ ID NO 21
<211> LENGTH: 42
<212> TYPE: DNA
<213> ORGANISM: Artificial
<220> FEATURE:
<223> OTHER INFORMATION: Epitope 3

<400> SEQUENCE: 21
gagtttgtgt tcagggtgct gatcccacgg atagcaagag tg                       42

<210> SEQ ID NO 22
<211> LENGTH: 14
<212> TYPE: PRT
<213> ORGANISM: Artificial
<220> FEATURE:
<223> OTHER INFORMATION: Epitope 3

<400> SEQUENCE: 22

Glu Phe Val Phe Arg Val Leu Ile Pro Arg Ile Ala Arg Val
1               5                   10
```